US006090838A

United States Patent [19]
Tang et al.

[11] Patent Number: 6,090,838
[45] Date of Patent: *Jul. 18, 2000

[54] METHODS AND COMPOSITIONS FOR INHIBITION OF ADAPTOR PROTEIN/ TYROSINE KINASE INTERACTIONS

[75] Inventors: Peng Cho Tang, Moraga; Gerald McMahon; G. Davis Harris, both of San Francisco, all of Calif.

[73] Assignee: Sugen, Inc., South San Francisco, Calif.

[*] Notice: This patent is subject to a terminal disclaimer.

[21] Appl. No.: 09/090,737

[22] Filed: Jun. 4, 1998

Related U.S. Application Data

[63] Continuation of application No. 08/658,337, Jun. 5, 1996, Pat. No. 5,780,496, which is a continuation-in-part of application No. 08/476,136, Jun. 7, 1995, abandoned.

[51] Int. Cl.[7] .......................... C07D 209/04; A61K 31/40
[52] U.S. Cl. ............................... 514/414; 548/455
[58] Field of Search .............................. 548/455; 514/414

[56] References Cited

U.S. PATENT DOCUMENTS 3,917,820  11/1975  Brewer et al. ........................... 424/122

FOREIGN PATENT DOCUMENTS 61-91167  5/1986  Japan .
63-60966  3/1988  Japan .

OTHER PUBLICATIONS

Marth J.D. et al., 1985, "A lymphocyte–specific protein–tyrosine kinase gene is rearranged and overexpessed in the murine T cell lymphoma LSTRA", *Cell* 43: 393–404.

Roebroek, A.J.M. et al., 1985, "The structure of the human c–fes/fps proto–oncogene", *EMBO J.* 4: 2897–2903.

Shtivelman, E. et al., 1986, "Alternative splicing of RNA's transcribed from the human abl gene and from the bcr–abl fused gene", *Cell* 47: 277–284.

Smith, M.R. et al., 1986, "Requirement for the c–ras proteins during viral oncogene transformation", *Nature* 320: 540–543.

Kruh, G.D. et al., 1986, "A novel human gene closely related to the abl proto–oncogene", *Science* 234: 1545–1548.

Horcher, J. et al., 1986, "Totalsynthese des Cochliodinols", *Liebigs Ann. Chem.* 10: 1765–1771.

Sadowski, I. et al., 1986, "A noncatalytic domain conserved among cytoplasmic protein–tyrosine kinases modifies the kinase function and transforming acitivty of Fujinami sarcoma virus p130gag/fps", *Mol. Cell Biol.* 6: 4396–4408.

Martinez R. et al., 1987, "Neuronal pp60c–src contains a six–amino acid insertion relative to its non–neuronal counterpart", *Science* 237: 411–414.

Sukegawa, J. et al., 1987, "Characterization of cDNA Clones for the Human c–yes Gene", *Mol. Cell. Biol.* 7:41–47.

McLaughlin, J. et al., 1987, "In vitro transformation of immature hematopoietic cells by the P210 BCR/ABL oncogene product of the Philadelphia chromosome", *Proc. Natl. Acad. Sci. USA* 84: 6558–6562.

Yamanishi Y. et al., 1987, "The yes–related cellular gene *lyn* encodes a possible tyrosine kinase similar to p56/ck", *Mol. Cell. Biol.* 7: 237–243.

Stahl et al., 1988, "Sequence similarity of phospholipase C with the non–catalytic region of src", *Nature* 332: 269–272.

Mayer, B.J. et al., 1988, "A novel viral oncogene with structural similarity to phospholipase C", *Nature* 332: 272–275.

Hanks et al., 1988, "The protein kinase family: conserved features and deduced phylogeny of the catalytic domains", *Science* 241: 42–52.

Lugo and Witte, 1989, "The BCR–ABL oncogene transforms Rat–1 cells and cooperates with v–myc", *Mol. Cell. Biol.* 9: 1263–1270.

Hao, Q. et al., 1989, "Isolation and sequence analysis of a novel human tyrosine kinase gene", *Mol. Cell. Biol.* 9: 1587–1593.

Morgan, D.O. et al., 1989, "Mitosis–specific phosphorylation of p60c–src by p34cdc2–associated protein kinase", *Cell* 57:775–786.

Nurse, O., 1990, "Universal control mechanism regulating onset of M–phase", *Nature* 344: 503–508.

Skehan et al., 1990, "New colorimetric cytotoxicity assay for anticancer–drug screening", *J. Natl. Cancer Inst.* 82:1107–1112.

Ullrich, A. and Schlessinger, J., 1990, "Signal transduction by receptors with tyrosine kinase activity", *Cell* 61:203–212.

Hardie, D.G., 1990, "Roles of protein kinases and phosphatases in signal transduction", *Symp. Soc. Exp. Biol.* 44:241–255.

Gibbs, J.B. et al., 1990, "Modulation of guanine nucleotides bound to Ras in NIH3T3 cells by oncogenes, growth factors, and the GTPase activating protein (GAP)", *J. Biol. Chem.* 265: 2037–2044.

Satoh, T. et al., 1990, "Platelet–derived growth factor stimulates formation of active p21ras–GTP complex in Swiss mouse 3T3 cells", *Proc. Natl. Acad. Sci. USA* 87: 5993–5997.

Kipreos, E.T. et al., 1990, "Differential phosphorylation of c–Abl in cell cycle determined by cdc2 kinase and phosphatase activity", *Science* 248: 217–220.

Dymecki, S.M. et al., 1990, "Specific expression of a tyrosine kinase gene, blk, in B lymphoid cells", *Science* 247: 332–336.

(List continued on next page.)

*Primary Examiner*—Zinna Northington Davis
*Attorney, Agent, or Firm*—Pennie & Edmonds LLP

[57] ABSTRACT

The present invention relates to methods and compositions for the inhibition of adaptor protein/protein tyrosine kinase protein interactions, especially wherein those interactions involving a protein tyrosine kinase capable of complexing with a member of the SH2- and/or SH3-containing family of adaptor proteins are associated with a cell proliferative disorder. Specifically, the present invention relates to particular compounds, especially quinazoline derivative compounds, and methods utilizing such compounds.

25 Claims, No Drawings

OTHER PUBLICATIONS

Muller, A.J. et al., 1991, "BCR first exon sequences specifically activate the BCR/ABL tyrosine kinase oncogene of Philadelphia chromosome–positive human leukemias", Mol. Cell. Biol. 11: 1785–1792.

Weaver et al., 1991, "CD8+ T–cell clones deficient in the expression of the CD45 protein tyrosine phosphatase have impaired responses to T–cell receptor stimuli", Mol. Cell. Biol., 11: 4415–4422.

Hunter T., 1991, "Cooperation between oncogenes", Cell 64: 249–270

Cantley, L.C. et al., 1991, "Oncogenes and signal transduction", Cell 64: 281–302.

Fischer, E.H. et al., 1991, "Protein tyrosine phosphatases: A diverse family of intracellular and transmembrane enzymes", Science 253: 401–406.

Koch C.A. et al., 1991, "SH2 and SH3 domains: Elements that control interactions of cytoplasmic signaling proteins", Science 252: 668–674.

Simon, M.I. et al., 1991, "Diversity of G proteins in signal transduction", Science 252: 802–808.

Kaziro, Y. et al., 1991, "Structure and function of signal–transducing GTP–binding proteins", Ann. Rev. Biochem. 60: 349–400.

Posada, J. and Cooper, J.A., 1992, "Molecular signal integration. Interplay between serine, threonine, and tyrosine phophorylation", Mol. Biol. Cell 3: 583–592.

Gishizky and Witte, 1992, "Initiation of deregulated growth of multipotent progenitor cells by bcr–abl in vitro", Science 256: 836–839.

Li, B.–Q. et al., 1992, "Nerve growth factor stimulation of the Ras–Guanine nucleotide exchange factor and GAP activities", Science 256: 1456–1459.

Sawyers et al., 1992, "Propogation of human myeloid leukemias in the SCID mouse", Blood 79: 2089–2098.

Schlessinger, J. and Ullrich, A., 1992, "Growth Factor Signalling by Receptor Tyrosine Kinases", Neuron 9: 383–391.

Scott, J.D. and Soderling, T.R., 1992, "Serine/threonine protein kinases", Current Opinion in Neurobiology 2: 289–295.

Lowenstein, E.J. et al., 1992, "The SH@ and SH3 domain–containing protein GRB2 links receptor tyrosine kinases to ras signaling", Cell 70: 431–442.

Pawson, T. and Gish, G., 1992, "SH2 and SH3 domains: From structure to function", Cell 71: 359–362.

Veillette, A. and Davidson, D., 1992, "Src–related protein tyrosine kinases and T–cell receptor signalling", TIG 8: 61–66.

Maness, P., 1992, "Nonreceptor protein tyrosine kinases associated with neuronal development", Dev. Neurosci. 14: 257–270.

Mayer, B.J. and Baltimore, D., 1993, "Signalling through SH2 and SH3 domains", Trends in Cell Biol. 3: 8–13.

Pawson, T. and Schlessinger, J., 1993, "SH2 and SH3 domains", Current Biology, 3: 434–442.

Lowy, D.R. and Willumsen, B.M., 1993, "Function and regulation of RAS", Ann. Rev. Biochem. 62: 851–891.

Medema, R.H. et al., 1993, "Ras activation by insulin and epidermal growth factor through enhanced exchange of guanine nucleotides on p21ras", Mol. Cell. Biol. 13: 155–162.

Buday, L. and Downward, J., 1993, "Epidermal growth factor regulates the exchange rate of Guanine nucleotides on p21ras in fibroblasts", Mol. Cell. Biol. 13: 1903–1910.

Simon, M.A. et al., 1993, "An SH3–SH2–SH3 protein is required for p21Ras1 activation and binds to Sevenless and Sos proteins in vitro", Cell 73: 169–177.

Olivier, J.P. et al., 1993, "A Drosophila SH2–SH3 adaptor protein implicated in coupling the Sevenless tyrosine kinase to an activator of Ras guanine nucleotide exchange, Sos", Cell 73: 179–191.

Buday, L. and Downward, J., 1993, "Epidermal growth factor regulates p21ras through the formation of a complex of receptor, Grb2 adaptor protein, and Sos nucleotide exchange factor", Cell 73: 611–620.

Egan, S.E. et al., 1993,"Association of Sos Ras exchange protein with Grb2 is implicated in tyrosine kinase signal transduction and transformation", Nature 363: 45–51.

Li, N. et al., 1993, "Guanine–nucleotide–releasing factor hSos1 binds Grb2 and links receptor tyrosine kinases to Ras signalling", Nature 363: 85–87.

Rozakis–Adock et al., 1993, "The SH2 and SH3 domains of mammalian Grb2 couple the EGF receptor to the Ras activator mSos1", Nature 363: 83–85.

Gale, N.W. et al., 1993, "Grb2 mediates the EGF–dependent activation of guanine nucleotide exchange on Ras", Nature, 363: 88–92.

Chardin, P. et al., 1993, "Human Sos1: a guanine nucleotide exchange factor for Ras that binds to GRB2" Science 260: 1338–1343.

Schlessinger, J., 1993, "How receptor tyrosine kinases activate Ras", TIBS 18: 273–275.

Matuoka et al., 1993, "Ash/Grb–2, a SH2/SH3–containing protein, couples to signalling for mitogenesis and cytoskeletal reorganization by EGF and PDGF", EMBO J. 12(9): 3467–3475.

Pendergrast, A.M. et al., 1993, "BCR–ABL–induced oncogenesis is mediated by direct interaction with the SH2 domain of the GRB–2 adaptor protein", Cell 75: 175–185.

van der Geer and Hunter, 1993, "Mutation of Tyr697, a GRB2–binding site, and Tyr721, a PI 3–kinase binding site, abrogates signal transduction by the murine CSF–1 receptor expressed in Rat–2 fibroblasts", EMBO J. 12(13): 5161–5172.

Schlaepfer et al., 1994, "Integrin–mediated signal transduction linked to Ras pathway by GBR2 binding to focal adhesion kinase", Nature 372: 786–791.

Li et al., 1994, "A new function for phosphotyrosine phosphatase: linking GRB2–Sos to a receptor tyrosine kinase", Mol. Cell Bio. 14(1): 509–517.

Levitzki and Gazit, 1995, "Tyrosine kinase inhibition: An approach to drug development", Science 267: 1782–1788.

Bu'Lock and Harley–Mason, 1951, "Melanin and Its Precursors. Part II, Model Experiments on the Reactions Between Quinones and Indoles, and Consideration of a Possible Structure for the Melanin Polymer", J. Chem. Soc. London, No. 152, pp. 703–712.

Colonna et al., 1962, Gazzetta Chimica Italiana 92: 1401–1421; (in Italian, Chem. Abstract) (CA) 59:542c, No. 1, Jul. 8, 1963 (in English).

Grazia Corradiniet al., 1989, "Acid– Catalyzed Reactions of Indoles with 1,4–quinones," Gazetta Chimica Italiana 119:153–156; (CA 111:232499, 1989).

Moehlau et al., Beilstein Reference 1–21–00–00420 of Chem. Ber., 44 (1911), pp. 3605–3619 (in German).

Yamamoto et al., 1988, "Preparation of indolylbenzoquinines as anti–cancer agents", JP 63–60966, in Japanese (Chem Abstr. 109(25):642 column 2, abstract no.:210891m). Certified English translation of JP 63–60966 included.

Young and Babbitt, 1982, "2–(2–Methyl–3–Indolyl)–1, 4–Benzoquinone, a Reversible Redox Substrate at the Carbon–Paste Electrode in Acidic Aqueous–Ethanolic Media", J. Org. Chem. 47:1571–1572 (Chem. Abstr. 96:151191w).

Arai, K., S. Shimizu, and Y. Yamamoto. 1981. Metabolic products of *Aspergillus Terreus*. VI. Metabolites of the Strain IFO 8835 (3). The isolation and chemical structures of colorless metabolites. Chem. Pharm. Bull. 29:1005–1012.

Arai, K. et al. 1981. Metabolic products of *aspergillus terreus*. IV. Metabolites of the strain IFO 8835. (2) The isolation and chemical structure of indolyl benzoquinone pigments. Chem. Pharm. Bull. 29:961–969.

Arai, K., S. Shimizu, Y. Taguchi, and Y. Yamamoto. 1981. Metabolic products of *aspergillus terreus*. V. Demethylation of asterriquinones. Chem. Pharm. Bull. 29:991–999.

Arai, K., and Y. Yamamoto. 1990. Metabolic products of *aspergillus terreus*. X. Biosynthesis of asterriquinones. Chem. Pharm. Bull. 38:2929–2932.

Brewer, D., W. A. Jerram, and A. Taylor. 1986. The production of cochliodinol and a related metabolite by chaetomium species. Canadian Journal of Microbiology 14:861–866.

Hörcher, U., E. Schwenner, and B. Franck. 1986. Totalsynthese des cochliodinols. Liebigs Ann. Chem. 1765–1771.

Jerram, W. A., A. G. McInnes, W. S. G. Maass, D. G. Smith, A. Taylor, and J. A. Walter. 1974, The chemistry of cochliodinol, a metabolite of chaetomium spp. Can. J. Chem. 53:727–737.

Kaji, A., N. Iwata, S. Wakusawa, and K.–i. Miyamoto. Aug. 1994. Four New Metabolites of *Aspergillus Terreus*. Chem. Pharm. Bull. 42:1682–1684.

Kaji, A. et al., Oct. 1995, Partial decetylation of asterriquinone diacetate by aqueous sodium bicarbonate in pyridine. Chem. Pharm. Bull. 43:1818–1820.

Meiler, D., and A. Taylor. 1970. The effect of cochliodinol, a metabolite of chaetomium chochliodes, on the respiration of microspores of fusarium oxysporum. Canadian Journal of Microbiology 17:83–86.

Mocek, U. et al., 1995. Isolation and structure elucidation of five new asterriquinones from *Aspergillus, Humicola and Botryotricum species*. Hauser Natural Products Chemistry Symposium—May 24, 1995.

O'Leary, A., and J. R. Hanson. 1982. Hinnuliquinone, A Bis–indolyl–2,5–dihyroxybenzoquinone pigment from nodulisporium hinnuleum. Tetrahedron Letters 23:1855–1856.

Ono, K., H. Nakane, S. Shimizu, and S. Koshimura. 1991. Inhibition of HIV–reverse transcriptase activity by asterriquinone and its analogues. Biochemical and Biophysical Research Communications 174:56–62.

Sekita, S. 1983. Isocochliodinol and neocochilodinol, Bis(3–indolyl)–benzoquinones from chaetomium spp. Chem. Pharm. Bull. 31:2998–3001.

Shimizu, S. and S Koshimura. 1990. Interaction of asterriquinone with deoxyribonucleic acid in vitro. Chem. Pharm Bull. 38:2617–19.

Shimizu, S., Y. Yamamoto, and S. Koshimura. 1982. Antitumor activity of asterriquinones from *Aspergillus Fungi*. IV. An attempt to modify the structure of asterriquinones to increase the activity. Chem. Pharm. Bull. 30:1896–1899.

Shimuzu, S., Y. Yamamoto, J.–i. Inagaki, and S. Koshimura. 1982. Antitumor effect and structure–activity relationship of asterriquinone analogs. Gann 73:642–648.

Yamamoto, Y., N. Kiriyama, S. Shimizu, and S. Koshimura. 1976. Antitumor Activity of Asterriquinone, A Metabolic Product from *Aspergillus Terreus*. Gann 67:623–624.

Yamamoto, Y., K.–i. Nishimura, and N. Kiriyama. 1976. Studies on the metabolic products of *aspergillus terreus*. I. metabolites of the strain IFO 6123. Chem. Pharm. Bull. 24:1853–1859.

METHODS AND COMPOSITIONS FOR INHIBITION OF ADAPTOR PROTEIN/ TYROSINE KINASE INTERACTIONS

This is a continuation, of application Ser. No. 08/658,337, filed Jun. 5, 1996, now U.S. Pat. No. 5,780,496, which is a continuation-in-part of application Ser. No. 08/476,136, filed Jun. 7, 1995 now abandoned.

1. INTRODUCTION

The present invention relates to methods and compositions for the inhibition of adaptor protein/phosphotyrosine interactions, especially wherein those interactions involve a protein tyrosine kinase capable of complexing with a member of the SH2 domain-containing family of adaptor proteins associated with a cell proliferative disorder. Specifically, the present invention relates to particular organic compounds, of methods utilizing such compounds.

2. BACKGROUND OF THE INVENTION

2.1 PROTEIN PHOSPHORYLATION AND SIGNAL TRANSDUCTION

Cells rely, to a great extent, on extracellular molecules as a means by which to receive stimuli from their immediate environment. These extracellular signals are essential for the correct regulation of such diverse cellular processes as differentiation, contractility, secretion, cell division, contact inhibition, and metabolism. The extracellular molecules, which can include, for example, hormones, growth factors, lymphokines, or neurotransmitters, act as ligands that bind to specific cell surface receptors. The binding of these ligands to their receptors triggers a cascade of reactions that brings about both the amplification of the original stimulus and the coordinate regulation of the separate cellular processes mentioned above. In addition to normal cellular processes, receptors and their extracellular ligands may be involved in abnormal or potentially deleterious processes such as virus-receptor interaction, inflammation, and cellular transformation to a cancerous state.

A central feature of this process, referred to as signal transduction (for recent reviews, see Posada, J. and Cooper, J. A., 1992, Mol. Biol. Cell 3:583–592; Hardie, D. G., 1990, Symp. Soc. Exp. Biol. 44:241–255), is the reversible phosphorylation of certain proteins. The phosphorylation or dephosphorylation of amino acid residues triggers conformational changes in regulated proteins that alter their biological properties. Proteins are phosphorylated by protein kinases and are dephosphorylated by protein phosphatases. Protein kinases and phosphatases are classified according to the amino acid residues they act on, with one class being serine-threonine kinases and phosphatases (reviewed in Scott, J. D. and Soderling, T. R., 1992, 2:289–295), which act on serine and threonine residues, and the other class being the tyrosine kinases and phosphatases (reviewed in Fischer, E. H. et al., 1991 Science 253:401–406; Schlessinger, J. and Ullrich, A., 1992, Neuron 9:383–391; Ullrich, A. and Schlessinger, J., 1990, Cell 61:203–212), which act on tyrosine residues. The protein kinases and phosphatases may be further defined as being receptors, i.e., the enzymes are an integral part of a transmembrane, ligand-binding molecule, or as non-receptors, meaning they respond to an extracellular molecule indirectly by being acted upon by a ligand-bound receptor. Phosphorylation is a dynamic process involving competing phosphorylation and dephosphorylation reactions, and the level of phosphorylation at any given instant reflects the relative activities, at that instant, of the protein kinases and phosphatases that catalyze these reactions.

While the majority of protein phosphorylation occurs at serine and threonine amino acid residues, phosphorylation at tyrosine residues also occurs, and has begun to attract a great deal of interest since the discovery that many oncogene products and growth factor receptors possess intrinsic protein tyrosine kinase activity. The importance of protein tyrosine phosphorylation in growth factor signal transduction, cell cycle progression and neoplastic transformation is now well established (Cantley, L. C. et al., 1991, Cell 64:281–302; Hunter T., 1991, Cell 64:249–270; Nurse, 1990, Nature 344:503–508; Schlessinger, J. and Ullrich, A., 1992, Neuron 9:383–391; Ullrich, A. and Schlessinger, J., 1990, Cell 61:203–212). Subversion of normal growth control pathways leading to oncogenesis has been shown to be caused by activation or overexpression of protein tyrosine kinases which constitute a large group of dominant oncogenic proteins (reviewed in Hunter, T., 1991, Cell 64:249–270).

2.2 PROTEIN TYROSINE KINASES

Protein tyrosine kinases comprise a large family of proteins, including many growth factor receptors and potential oncogenes, which share ancestry with, but nonetheless differ from, serine/threonine-specific protein kinases (Hanks et al., 1988, Science 241:42–52).

Receptor-type protein tyrosine kinases having a transmembrane topology have been studied extensively. The binding of a specific ligand to the extracellular domain of a receptor protein tyrosine kinase is thought to induce receptor dimerization and phosphorylation of their own tyrosine residues. Individual phosphotyrosine residues of the cytoplasmic domains of receptors may serve as specific binding sites that interact with a host of cytoplasmic signalling molecules, thereby activating various signal transduction pathways (Ullrich, A. and Schlessinger, J., 1990, Cell 61:203–212).

The intracellular, cytoplasmic, non-receptor protein tyrosine kinases, may be broadly defined as those protein tyrosine kinases which do not contain a hydrophobic, transmembrane domain. Within this broad classification, one can divide the known cytoplasmic protein tyrosine kinases into eleven distinct morphotypes, including the SRC family (Martinez, R. et al., 1987, Science 237:411–414; Sukegawa, J. et al., 1987, Mol. Cell. Biol., 7:41–47; Yamanishi, Y. et al., 1987, 7:237–243; Marth, J. D. et al., 1985, Cell 43:393–404; Dymecki, S. M. et al., 1990, Science 247:332–336), the FES family (Ruebroek, A. J. M. et al., 1985, EMBO J. 4:2897–2903; Hao, Q. et al., 1989, Mol. Cell. Biol. 9:1587–1593), the ABL family (Shtivelman, E. et al., 1986, Cell 47:277–284; Kruh, G. D. et al., 1986, Science 234:1545–1548), the $Za_p$ 70 family and the JAK family. While distinct in their overall molecular structure, each of the members of these morphozypic families of cytoplasmic protein tyrosine kinases share non-catalytic domains in addition to sharing their catalytic kinase domains. Such non-catalytic domain are the SH2 (SRC homology domain 2; Sadowski, I. et al., Mol. Cell. Biol. 6: 4396–4408; Koch, C. A. et al., 1991, Science 252:668–674) domains and SH3 domains (Mayer, B. J. et al., 1988, Nature 332:269–272). Such non-catalytic domains are thought to be important in the regulation of protein-protein interactions during signal transduction (Pawson, T. and Gish, G., 1992, Cell 71:359–362).

While the metabolic roles of cytoplasmic protein tyrosine kinases are less well understood than that of the receptor-type protein tyrosine kinases, significant progress has been made in elucidating some of the processes in which this class of molecules is involved. For example, members of the src family, lck and fyn, have been shown to interact with CD4/CD8 and the T cell receptor complex, and are thus implicated in T cell activation, (Veillette, A. and Davidson, D., 1992, TIG 8:61–66), certain cytoplasmic protein tyrosine kinases have been linked to certain phases of the cell cycle (Morgan, D. O. et al., 1989, Cell 57: 775–786; Kipreos, E. T. et al., 1990, Science 248: 217–220; Weaver et al., 1991, Mol. Cell. Biol. 11:4415–4422), and cytoplasmic protein tyrosine kinases have been implicated in neuronal development (Maness, P., 1992, Dev. Neurosci 14:257–270). Deregulation of kinase activity through mutation or overexpression is a well-established mechanism underlying cell transformation (Hunter et al., 1985, supra; Ullrich et al., supra).

2.3 ADAPTOR PROTEINS

Adaptor proteins are intracellular proteins having characteristic conserved peptide domains (SH2 and/or SH3 domains, as described below) which are critical to the signal transduction pathway. Such adaptor proteins serve to link protein tyrosine kinases, especially receptor-type protein tyrosine kinases to downstream intracellular signalling pathways such as the RAS signalling pathway. It is thought that such adaptor proteins may be involved in targeting signal transduction proteins to the correct site in the plasma membrane or subcellular compartments, and may also be involved in the regulation of protein movement within the cell.

Such adaptor proteins are among the protein substrates of the receptor-type protein tyrosine kinases, and have in common one or two copies of an approximately 100 amino acid long motif. Because this motif was originally identified in c-Src-like cytoplasmic, non-receptor tyrosine kinases it is referred to as a Src homology 2 (SH2) domain. SH2-containing polypeptides may otherwise, however, be structurally and functionally distinct from one another (Koch, C. A. et al., 1991, Science 252:668–674). SH2 domains directly recognize phosphorylated tyrosine amino acid residues. The peptide domains also have independent sites for the recognition of amino acid residues surrounding the phosphotyrosine residue(s).

When a receptor protein tyrosine kinase binds an extracellular ligand, receptor dimerization is induced, which, in turn, leads to intermolecular autophosphorylation of the dimerized kinases (Schlessinger, J. and Ullrich, A., 1992, Neuron 9: 383–391). Receptor phosphorylation, therefore, creates SH2-binding sites, to which an adaptor protein may bind.

In addition to SH2 peptide domains, many of the adaptor proteins involved in signal transduction contain a second conserved motif of 50–75 amino acids residues, the SH3 domain (Schlessinger, J. and Ullrich, A., 1992, Neuron 9:383–391; Pawson, T. and Gish, G. D., 1992, Cell 72:359–362; Mayer, B. J. and Baltimore, D., 1993, Trends in Cell Biol. 3 8–13; Mayer, B. J. et al., 1988, Nature 352:272–275). Much less is known about the biological role of the SH3 domain than is known about the role of SH2. The current view is that SH3 domains function, in part, as protein-binding domains that act to link signals transmitted from the cell surface to downstream effector genes such as ras (Pawson, T. and Schlessinger, J., 1993 Current Biology, 3:434–442).

2.4 G-PROTEINS AND SIGNAL TRANSDUCTION

Guanine-nucleotide-binding proteins, (G-proteins; Simon, M. I. et al., 1991, Science 252:802–808; Kaziro, Y. et al., 1991, Ann. Rev. Biochem. 60:349–400) such as Ras (for review, see Lowy, D. R. and Willumsen, B. M., 1993, Ann Rev. Biochem. 62:851–891), play an essential role in the transmission of mitogenic signals from receptor tyrosine kinases. Taking Ras as an example, the activation of receptor tyrosine kinases by ligand binding results in the accumulation of the active GTP bound form of the Ras molecule (Gibbs, J. B. et al., 1990, J. Biol. Chem. 265:20437–2044; Satoh, T. et al., 1990, Proc. NaTl. Acad. Sci. USA 87:5993–5997; Li, B.-Q. et al., 1992, Science 256:1456–1459; Buday, L. and Downward, J., 1993, Mol. Cell. Biol. 13:1903–1910; Medema, R. H. et al., 1993, Mol. Cell. Biol. 13:155–162). Ras activation is also required for transformation by viral oncogenic tyrosine kinases (Smith, M. R. et al., 1986, Nature 320:540–43).

Ras activity is regulated by the opposing actions of the GTPase-activating proteins (GAPs) and guanine nucleotide exchange factors, with GAPs stimulating the slow intrinsic rate of GTP hydrolysis on Ras and exchange factors stimulating the basal rate of exchange of GDP for GTP on Ras. Thus, GAPs act as negative regulators of Ras function, while exchange factors act as Ras activators.

Recently, a direct link between activated receptor tyrosine kinases and Ras was established with the finding that the mammalian GRB-2 protein, a 26 kilodalton protein comprised of a single SH2 and two SH3 domains (Lowenstein, E. J. et al., 1992, Cell 70:431–442), directly couples receptor tyrosine kinases to the Ras exchange factor Sos in mammals and Drosophila (Buday, L. and Downward, J., 1993, Cell 73:611–620; Egan, S. E. et al. 1993, Nature 363:45–51; Li, N. et al., 1993, Nature 363:85–87; Gale, N. W. et al., 1993, Nature 363:88–92; Rozakis-Adcock et al., 1993, Nature 363:83–85; Chardin, P. et al., 1993, Science 260:1338–1343; Oliver, J. P. et al., Cell 73:179–191; Simon, M. A. et al., 1993, Cell 73:169–177). The GRB-2 SH2 domain binds to specific tyrosine phosphorylated sequences in receptor tyrosine kinases while the GRB-2 SH3 domains bind to proline-rich sequences present in the Sos exchange factor. Binding of GRB-2 to the receptor kinases, therefore, allows for the recruitment of Sos to the plasma membrane, where Ras is located (Schlessinger, J., 1993, TIBS 18:273–275).

Grb2 has been shown to be associated with CSF-1 receptor (vanderGeer and Hunter, 1993, EMBO J. 12(13):5161–5172), PDGF receptor (Li et al., 1994, MCB 14(1):509–517), EGF-R (Matuoka et al., 1993, EMBO J. 12(9):3467–3475; Lowenstein et al., 1992, Cell 70:431–442) and Fak (Schlaepfer et al., 1994, Nature 372:786–791), amongst other proteins.

2.5 CELL PROLIFERATIVE DISORDERS

Growth factors and their receptors are crucial for normal development but can also act as oncogenes leading to cell transformation, oncogenesis, and cell proliferative disorders, including cancer. Activation of the oncogenic potential of normal cellular proteins such as protein tyrosine kinases may, for example, occur by alteration of the proteins' corresponding enzymatic activities, their inappropriate binding to other cellular components, or both.

Taking as an example Philadelphia chromosome-positive human leukemias, it is known that the BCR-ABL oncoprotein is involved in the pathenogenesis of such leukemias. BCR-ABL exhibits deregulated tyrosine kinase activity. It has recently been demonstrated (Pendergast, A. M. et al., 1993, Cell 75:175–185) that BCR-ABL binds the SH2/SH3 domain-containing GRB-2 adaptor protein. Further, it has been demonstrated that BCR-ABL/GRB-2 binding is mediated by the direct interaction the GRB-2 SH2 domain and a tyrosine-phosphorylated region of the BCR-ABL protein, and that this interaction is required for the activation of the Ras signaling pathway.

Thus, there are multiple events which occur along a signal transduction pathway which appear to be required for the ultimate appearance of a cell proliferative disorder such as the form of leukemia described above. One approach to the treatment of oncogenenic, cell proliferative disorders would be to attempt to "short circuit" abnormal signal transduction events which contribute to the appearance of such disorders, by interfering with one or more of these requisite events.

The amelioration of an abnormal kinase activity may be interfered with by targeting and directly inhibiting the enzymatic activity of the kinase involved in the cell proliferative disorder. It has been proposed that certain compounds may have such anti-tyrosine kinase activity. See, for example, Levitzki and Gazit, 1995, Science 267:1782–1788, wherein certain quinazoline derivatives are proposed to directly inhibit receptor tyrosine kinase enzymatic activity.

In instances wherein the signal transduction event of interest involves an adaptor protein/protein tyrosine kinase interaction, the inhibition of such interactions may lead to the amelioration of cell proliferative disorder symptoms. The utility of this approach has been demonstrated using expression of signaling incompetent proteins in cells. For example, cells expressing a mutant form of Bcr-Ab1 which lacks the tyrosine residue necessary for binding of the GrB2 SH2 domain and is thus signaling incompetent no longer exhibits a transformed phenotype (RER) (Pendergast et al., supra). To date, however, no such inhibitor of adaptor protein/protein tyrosine kinase interactions has been identified.

3. SUMMARY OF THE INVENTION

The present invention relates to methods and compositions for the inhibition of adaptor protein/protein tyrosine kinase protein interactions, especially wherein those interactions involving a protein tyrosine kinase capable of complexing with a member of the SH2- and/or SH3-containing family of adaptor proteins are associated with a cell proliferative disorder. Specifically, the present invention relates to particular organic compounds and methods utilizing such compounds.

"Protein tyrosine kinase" will, herein, be abbreviated "PTK". It is to be understood that "PTK" may refer to either a transmembrane, receptor-type protein tyrosine kinase or a cytoplasmic protein tyrosine kinase, unless otherwise indicated. The compounds of the invention inhibit PTK/adaptor protein interactions, especially PTK/adaptor protein interactions wherein the PTK is, for example, an epidermal growth factor receptor (EGF-R) protein tyrosine kinase molecule, a platelet derived growth factor receptor (PDGF-R) protein tyrosine kinase molecule, or an insulin growth factor-like receptor tyrosine kinase molecule (IGF-1R).

The compounds of the present invention are described by the formula (I) below:

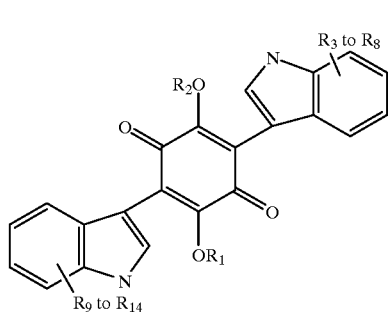

(I)

and pharmaceutically acceptable salts thereof, wherein:

R1 and R2 are independently H, acetate or aryl, alkylaryl and higher alkyl acid ester;

R3 to R14 are independently H, alkyl, alkenyl, alkynyl, OH, hydroxyalkyl, alkoxy, nitro, halo, trihalomethyl, amide, carboxamide, carboxy, sulfonyl, sulfonamide, amino, and mercapto which can be substituted or substituted where appropriate.

Specific compounds within the scope of the present invention are described by the formula (II) below. R1 and R2 of the formula can be as listed in Table I following the formula. Illustrative preparations or isolations of these compounds are found in the working examples.

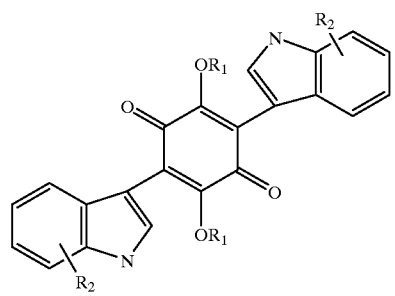

(II)

TABLE I

| Example | R1 | R2 |
|---|---|---|
| 1. | H | 2-(2-methylbut-2-en-4-yl) |
| 2. | acetyl | 2-(2-methylbut-2-en-4-yl) |
| 3. | acetyl | 2-(3-methyl-n-butyl) |
| 4. | H | 2-(3-methyl-n-butyl) |
| 5. | H | 5-bromo |
| 6. | H | 2-allyl |
| 7. | H | 2-n-propyl |
| 8. | H | 2-aminocarbonyl |
| 9. | acetyl | 2-aminocarbonyl |
| 10. | benzoyl | 2-allyl |
| 11. | H | 2-cyano |
| 12. | H | 4-methoxycarbonyl |
| 13. | H | 5,7-dimethoxy |
| 14. | H | 4,7-dimethoxy |
| 15. | H | 5-nitro |
| 16. | H | 4-(4-chlorobenzoylamino) |
| 17. | H | 4-(4-chlorophenyl) |
| 18. | H | 2-(4-fluorophenyl) |
| 19. | H | 4,6-dimethoxy |
| 20. | H | 5-hydroxy-6-methoxy |
| 21. | H | 4-cyano |
| 22. | H | 5-(4-trifluoromethylphenyl-aminocarbonyl) |
| 23. | H | 2-(4-trifluoromethylphenyl-aminocarbonyl) |
| 24. | H | 2-ethyl |
| 25. | H | 5-bromo-6-nitro |
| 26. | OMe | 2-(2-methylbut-2-en-4-yl) |
| 27. | OMe | 2-(3-methyl-n-butyl) |

Specific compounds within the scope of the present invention are also described by formula (III) below. R1–R12 of the formula can be as listed in Table II following the formula. Illustrative preparations or isolations of these compounds are found in the working examples.

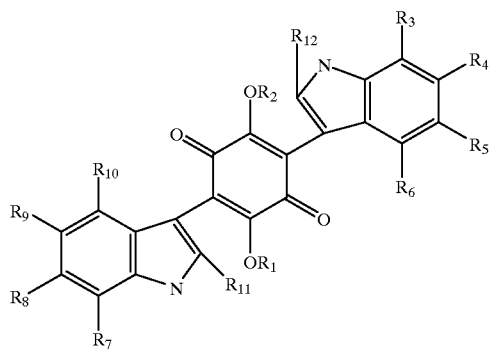

(III)

TABLE II

| Ex. | R1 = R2 | R11 | R12 | R3–R10[1] |
|---|---|---|---|---|
| 28. | H | 2-(3-methyl-n-butyl) | 2-(3-methyl n-butyl) | |
| 29. | H | 2-methyl | 2-methyl | |
| 30. | H | 2-ethyl | 2-ethyl | |
| 31. | H | 2-butyl | 2-butyl | |
| 32. | H | 2-(but-1-en-4-yl) | 2-(but-1-en-4-yl) | |
| 33. | H | 2-(4-methyl-n-pentyl) | 2-(4-methyl-n-pentyl) | |
| 34. | H | 2-phenylethyl | 2-phenylethyl | |
| 35. | H | H | 2-(3-methyl n-butyl) | |
| 36. | H | 2-ethyl | 2-ethyl | R5 = R9 = carboxy |
| 37. | H | 2-(n-propyl) | 2-(n-propyly) | R5 = R9 = carboxy |
| 38. | H | 2-(3-methyl-n-butyl) | 2-(3-methyl-n-butyl) | R5 = R9 = carboxy |
| 39. | H | 2-(4-carboxy-n-butyl) | 2-(4-carboxy-n-butyl) | |
| 40. | H | H | 2-(3-methyl-n-butyl) | R5 = carboxy |
| 41. | H | 2-ethyl | 2-ethyl | R5 = R9 = amino |
| 42. | H | 2-(n-propyl) | 2-(n-propyl) | R5 = R9 = amino |
| 43. | H | 2-(3-methyl-n-butyl) | 2-(3-methyl n-butyl) | R5 = R9 = amino |
| 44. | acetyl | 2-(3-methyl-n-butyl) | 2-(3-methyl-n-butyl) | |
| 45. | H | 2-ethyl | 2-ethyl | R5 = R9 = (4-methylphenyl-sulfonylamino) |
| 46. | H | 2-(n-propyl) | 2-(n-propyl) | R5 = R9 = (4-methylphenyl-sulfonylamino) |
| 47. | H | 2-(3-methyl-n-butyl) | 2-(3-methyl-n-butyl) | R5 = R9 = (4-methylphenyl-sulfonylamino) |
| 48. | H | 2-(2-methylbut-1-en-4-yl) | 2-(2-methylbut-1-en-4-yl) | |
| 49. | H | 2-(2-methylpent-2-en-5-yl) | 2-(2-methylpent-2-en-5-yl) | |

[1]Unless otherwise indicated, R3–R10 = hydrogen.

By the term "alkyl" as used herein is meant a straight or branched chain saturated hydrocarbon group having from 1 to 20 carbons such as methyl, ethyl, isopropyl, n-butyl, s-butyl, t-butyl, n-amyl, isoamyl, n-hexyl, n-octyl and n-decyl; "alkenyl" and "alkynyl" are used to mean straight or branched chain hydrocarbon groups having from 2 to 10 carbons and unsaturated by a double or triple bond respectively, such as vinyl, allyl, propargyl, 1-methylvinyl, but-1-enyl, but-2-enyl, but-2-ynyl, 1 methylbut-2-enyl, pent-1-enyl, pent-3-enyl, 3-methylbut-1-ynyl, 1,1-dimethylallyl, hex-2-enyl and 1-methyl-1-ethylallyl; "alkylaryl" means the aforementioned alkyl groups substituted by a phenyl group such as benzyl, phenethyl, phenopropyl, 1-benzylethyl, phenobutyl and 2-benzylpropyl; "aryl" as used herein includes a monocyclic or bicyclic rings, wherein at least one ring is aromatic including aromatic or heteroaromatic hydrocarbons; the term "hydroxy-alkyl" means the aforementioned alkyl groups substituted by a single hydroxyl group such as 2-hydroxyethyl, 2-hydroxypropyl, 3-hydroxypropyl, 4-hydroxybutyl, 1-hydroxybutyl and 6-hydroxyhexyl.

The term "substituted" as used herein means that the group in question may bear one or more substituents including but not limited to halogen, hydroxy, cyano, alkyl, aryl, alkenyl, alkynyl, amino, nitro, mercapto, carboxy and other substituents known to those skilled in the art.

Preferred compounds of the present invention include the following:

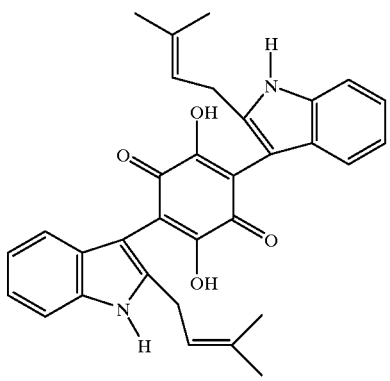

Compound 1

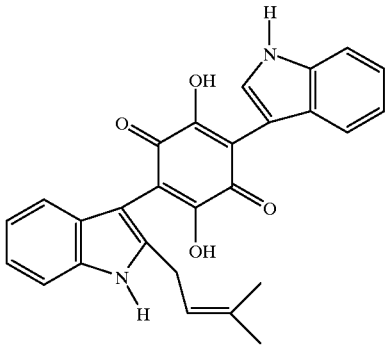

Compound 2 and pharmaceutically acceptable salts thereof.

In addition, the present invention encompasses a pharmaceutical composition comprising a compound of the invention, and methods for using a compound or pharmaceutical composition of the invention in an animal, particularly a human, to ameliorate symptoms of cell proliferative disorders involving protein tyrosine kinase/adaptor protein interactions.

This invention is based, in part, on the discovery that the disclosed compounds, while exhibiting no inhibitory effect on protein tyrosine kinase enzymatic activity, act to inhibit the binding of an SH2-containing peptide to a tyrosine phosphorylated EGF receptor. The data representing this discovery is presented in the Examples in Sections 6, 7 and 8, below. The Example presented in Section 5, below, describes a method for the production of the compounds of the present invention.

The present invention represents the first instance whereby compounds have been discovered which directly inhibit the interaction between adaptor proteins and protein tyrosine kinase molecules.

4. DETAILED DESCRIPTION OF THE INVENTION

Described below are methods and compositions for the inhibition of adaptor protein/protein tyrosine kinase protein interactions, especially those interactions associated with a cell proliferative disorder. Specifically, described below are particular organic compounds, methods for the synthesis of such compounds, and techniques utilizing such compounds.

4.1 COMPOUNDS

The compounds of the present invention are described by the following formula (IV):

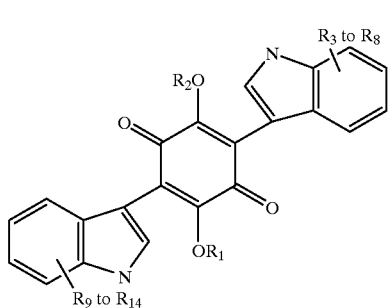

(IV)

and pharmaceutically acceptable salts thereof, wherein:
R1 and R2 are independently H, acetate or aryl, alkylaryl and higher alkyl acid ester;
R3 to R14 are independently H, alkyl, alkenyl, alkynyl, hydroxyalkyl, OH, alkoxy, nitro, halo, trihalomethyl, amide, carboxamide, carboxy, sulfonyl, sulfonamide, amino, and mercapto which can be unsubstituted or substituted where appropriate. For example, alkyl groups of the compounds of the present invention may be substituted where appropriate with one or more carboxy or aryl groups. Alkenyl groups of compounds of the present invention may be substituted where appropriate with one or more carboxy groups. Specific compounds within the scope of the present invention are found in the preceding Tables I and II. Illustrative preparations or isolations of these compounds are found in the working examples.

In one embodiment, compounds of the present invention are described by the following formula (III):

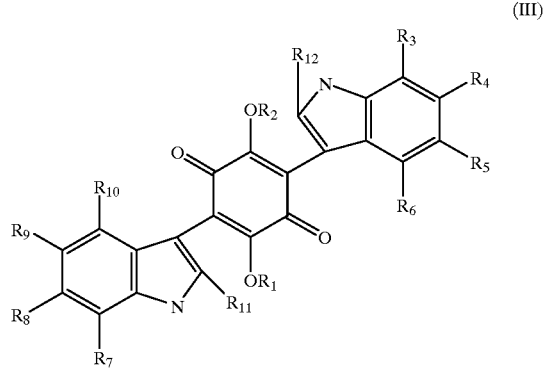

(III)

and pharmaceutically acceptable salts thereof, wherein:
R1 and R2 are each independently hydrogen, lower alkyl, acetyl, aryl, alkylaryl or higher alkyl acid ester, and wherein at least one of R1 and R2 is other than hydrogen;

R3 to R12 are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, mercapto or 2-methylbut-2-en-4-yl; and wherein at least one of R11 and R12 is 2-methylbut-2-en-4-yl.

Groups R1–R12 may be substituted or unsubstituted where appropriate.

In another embodiment, compounds of the present invention are described by formula (III) above, and pharmaceutically acceptable salts thereof, wherein:
R1 and R2 are both H;
R3 to R10 are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, mercapto or 2-methylbut-2-en-4-yl; and
R11 and R12 are each independently H or 2-methylbut-2-en-4-yl, wherein at least one of R11 and R12 is 2-methylbut-2-en-4-yl;
wherein at least one of R3 to R10 is other than H.

In another embodiment, compounds of the present invention are described by formula (III) above, and pharmaceutically acceptable salts thereof, wherein:
R1 and R2 are each independently aryl, alkylaryl and higher alkyl acid ester; and
R3 to R12 are each independently H, alkyl, alkylcarboxy, alkenyl, alkenylcarboxy, aryl, alkylaryl, OH, alkoxy, nitro, fluoro, chloro, iodo, trihalomethyl, amide, carboxamide, carboxy, sulfonyl, sulfonamide, amino, or mercapto.

In another embodiment, compounds of the present invention are described by formula (III) above, and pharmaceutically acceptable salts thereof, wherein:
R1, R2, R11 and R12 are H; and
R3 to R10 are each independently H, alkyl, alkylcarboxy, alkenyl, alkenylcarboxy, aryl, alkylaryl, alkoxy, hydroxy, nitro, halo, trihalomethyl, amide, carboxamide, carboxy, sulfonyl, sulfonamide, amino, or mercapto, wherein at least one of R3 to R10 is other than H;
(a) when R4–R10 are each H, R3 may not be 2-methylbut-2-en-4-yl or 2-hydroxy-2-methylbut-4-yl;
(b) when R4–R6 and R8–R10 are each H, R3 and R7 may not simultaneously be 2-methylbut-2-en-4-yl;
(c) when R3–R4, R6–R8 and R10 are H, R5 and R9 may not simultaneously be 2-methylbut-2-en-4-yl or 3-methyl-n-butyl;
(d) when R3, R5–R7, R9–R10 are H, R4 and R8 may not both be 2-methylbut-2-en-4-yl or 2-methylbut-1,4-dien-4-yl, and R4 and R8 may not be 2-methylbut-2-en-4-yl and 2-methylbut-1,4-dien-4-yl.

The present invention also encompasses compounds of formula (III) above, and pharmaceutically acceptable salts thereof, wherein R3–R5 and R7–R9 are H and either or both of R6 and R 10 are 2-methylbut-2-en-4-yl.

In another embodiment, compounds of the present invention are described by formula (III) above, and pharmaceutically acceptable salts thereof, wherein:
at least one of R1 and R2 is acetyl;
R11 a nd R12 are H; and
R3 to R10 are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, and mercapto, wherein:
(a) when both R1 and R2 are acetyl; or when one of R1 and R2 is acetyl and R3–R4, R6–R8 and R10–R12 are H; R5 and R9 may not simultaneously be 2-methylbut-2-en-4-yl;
(b) when both R1 and R2 are acetyl and when R4–R6 and R8–R10 are H, R3 and R7 may not simultaneously be 2-methylbut-2-en-4-yl;
(c) when both R1 and R2 are acetyl and when R3, R5–R7, and R9–R10 are H, R4 and R8 may not simultaneously be 2-methylbut-2-en-4-yl.

In another embodiment, compounds of the present invention are described by formula (III) above, and pharmaceutically acceptable salts thereof, wherein:
at least one of R1 and R2 is lower alkyl;
R11 and R12 are H; and
R3 to R10 are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, and mercapto, wherein:
(a) when both R1 and R2 are methyl, at least one of R3 to R10 must be a group other than H;
(b) when both R1 and R2 are methyl, and R4–R10 are H, R3 may not be 2-methylbut-2-en-4-yl;
(c) when both R1 and R2 are methyl, and R4–R6 and R8–R10 are H, R3 and R7 may not simultaneously be 2-methylbut-2-en-4-yl;
(d) when both R1 and R2 are methyl, and R3–R4, R6–R8 and R10 are H, R5 and R9 may not simultaneously be 2-methylbut-2-en-4-yl.

The present invention also includes compounds of formula III) above, and pharmaceutically acceptable salts thereof,
wherein R4 is 2-methylbut-2-en-4-yl and R3 and R5–R10 are H;
or R5 is 2-methylbut-2-en-4-yl and R3–R4 and R6–R10 are H;
or R6 is 2-methylbut-2-en-4-yl, and R3–R5 and R7–R10 are H.

In another embodiment, compounds of the present invention are described by formula (III) above, and pharmaceutically acceptable salts thereof, wherein:
R1 and R2 are each independently hydrogen, lower alkyl, acetyl, aryl, alkylaryl or higher alkyl acid ester,
R3 to R10 are each independently H, alkyl, alkylcarboxy, aryl, alkylaryl, alkenyl, alkenylcarboxy, OH, alkoxy, nitro, halo, trihalomethyl, amide, carboxyamide, carboxy, sulfonyl, sulfonamide, amino, mercapto, 4-methylphenylsulfonylamino, or 2-methylbut-2-en-4-yl; and
R11 and R12 are selected from the group consisting of hydrogen, methyl, ethyl, propyl, butyl, aryl, alkylaryl, alkylcarboxy, alkenylcarboxy, but-1-en-4-yl, 2-methylbut-1-en-4-yl, 4-methyl-n-pentyl, 2-phenylethyl, 2- methylpent-2-en-4-yl, and 4-carboxy-n-butyl, wherein at least one of R11 and R12 is other than hydrogen.

In yet another embodiment, compounds of the present invention are described by formula (III) above, and pharmaceutically acceptable salts thereof, wherein:
R1 and R2 are each independently hydrogen, lower alkyl, acetyl, aryl, alkylaryl or higher alkyl acid ester,
R3 to R10 are each independently H, alkyl, alkylcarboxy, aryl, alkylaryl, alkenyl, alkenylcarboxy, OH, alkoxy, nitro, halo, trihalomethyl, amide, carboxyamide, carboxy, sulfonyl, sulfonamide, amino, mercapto, 4-methylphenylsulfonylamino, or 2-methylbut-2-en-4-yl; and
R11 and R12 are both 3-methyl-n-butyl.

In still another embodiment, compounds of the present invention are described by formula (III) above, and pharmaceutically acceptable salts thereof, wherein:
R1 and R2 are each independently hydrogen, lower alkyl, acetyl, aryl, alkylaryl or higher alkyl acid ester,
R3 to R10 are each independently H, alkyl, alkylcarboxy, aryl, alkylaryl, alkenyl, alkenylcarboxy, OH, alkoxy, nitro, halo, trihalomethyl, amide, carboxyamide, carboxy, sulfonyl, sulfonamide, amino, mercapto, 4-methylphenylsulfonylamino, or 2-methylbut-2-en-4-yl and wherein at least one of R3 to R10 is other than hydrogen; and
R11 and R12 are each independently hydrogen or 3-methyl-n-butyl.

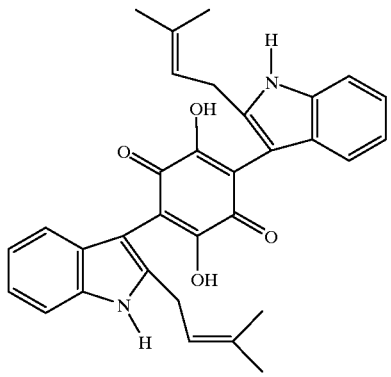

Compound 1

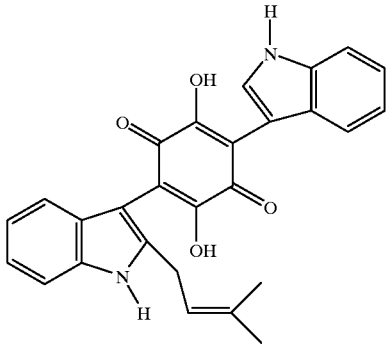

Compound 2

The invention encompasses the compounds described above as well as pharmaceutically acceptable salts thereof. The compounds of the present invention can either be synthesized or isolated as described herein.

The compounds of the present invention can be synthesized in accordance with standard organic chemistry techniques using readily available starting materials. Alternatively, the compounds can be isolated as described in Section 5.2, below. Chemical synthesis and isolation methods are provided herein solely for illustration. Variation of these methods will be apparent to those skilled in the art.

4.2 PRODUCTION OF THE COMPOUNDS
4.2.1 ISOLATION OF NATURAL PRODUCTS

The present Example employed a fungus culture (PenLabs Inc. #592), and the following fermentation conditions: medium yeast malt extract plus trace elements at 22° C. The seed medium consisted of mannitol 60.0 g; soybean meal 12.5 g, citric acid 2.5 g, yeast extract 0.5 g, and $H_2O$ to 1 liter. The pH of the seed medium was adjusted to 7.0 before autoclaving. 30 mL seed medium were dispensed per 250 ml flask (6 days 28° C.), which was then inoculated with 1 ml of spore/mycelium homogenate suspension (2 days). Stock cultures were maintained frozen at −80° C. in spore storage solutions.

The fermentation mixture (mycelium and broth) was homogenized and filtered through cheesecloth by suction filtration. The filtrate was extracted three times with 0.5 v/v of ethyl acetate. The ethyl acetate layers were combined and the solvent removed by rotary evaporation. The mycelium was extracted twice with 0.4 v/v of ethyl acetate. The ethyl acetate layers were combined and the solvent removed by rotary evaporation. The oily residues both containing the asterriquinones were combined and dried on a vacuum pump overnight.

The crude extract obtained above underwent CPC fractionation on a PC Inc. high speed countercurrent chromatograph (HSCC) containing a "tripple" coil column. A 1:3:3:3 v/v/v/v of n-hexane, ethyl acetate, methanol and water was mixed and allowed to settle overnight. The lower layer was pumped into HSCC column as the stationary phase. The upper layer was used as the mobile phase. After two hours, the lower and upper layer were switched. The HSCC run was completed after four hours. The crude metabolites eluted from 8 to 12 minutes. The active fractions were pooled and evaporated under reduced pressure to dryness.

The pooled HSCC fraction (8-12) was subjected to semi-preparative HPLC (Water HPLC system with a Water 996 photodioarray detector using Millennium software) fractionations using the following conditions:

Two semi-preparative $C_{18}$-cartridges (25×100 mm each, Nova Pak, 6μ); Flow rate: 10 mL/min.; 120 mg of the pooled HSCC fraction 8-12 dissolved in 6 mL of DMSO; 250 μL aliquots per injection; PDA monitored at 270 nm; linear gradient of 70% $H_2O$/30% $CH_3CN$ to 100% $CH_3CN$ over 30 minutes; then isocratic at 100% $CH_3CN$ for 6 minutes; the active material eluted at 19 and 24 minutes. The active fractions from the 10 runs were combined and evaporated under reduced pressure to dryness to yield 17 mg of Asterriquinone C-3 (Compound I) and 3 mg of Preasterriquinone C-3 (Compound II).

Mass spectra were recorded on PE Sciex LC-MS model API III (Ion Spray), exact mass measurements were performed at high resolution (HR-FAD). Mass spectral analysis for compound I gave a molecular ion of 507 $(M+H)^+$ (molecular weight: 506). The molecular formula $C_{32}H_{31}N_2O_4(M^++H)$: 507.2289; found 507.2291). $^1H$ NMR spectra of compound I were recorded in $CDCl_3$ at 500 MHz on a Brucker DRX-500. Chemical shifts are given in ppm relative to TMS at zero ppm using the solvent peak at 7.26 ppm ($CDCl_3$) as an internal standard. Compound I: 8.18 (s, 2H), 8.05 (s, 2H), 7.35–7.10 (m, 8H), 5.40 (m, 2H), 3.45 (m, 4H), 1.81 (s, 6H) and 1.75 ppm (s, 6H). $^{13}C$ NMR spectra of compound I were recorded in DMSO-$d_6$ at 125 MHz on a Brucker DRX-500. Chemical shifts are given in ppm relative to TMS at zero using the solvent peak at 39.5 ppm (DMSO-$d_6$) as an internal standard. 138.8, 136.6, 136.3, 128.8, 128.2, 127.3, 122.3, 121.8, 121.0, 120.3, 119.5, 119.3, 112.3, 111.8, 111.6, 105.2, 102.2, 27.3, 26.4 and 18.5 ppm. Compound I gave a melting point of 150–154° C.

Mass spectral analysis for compound II gave a molecular ion of 439 $(M+H)^+$ (molecular weight: 438). $^1H$ NMR spectra of compound II were recorded in DMSO-$d_6$ at 500 MHz on a Brucker DRX-500. Chemical shifts are given in ppm relative to TMS at zero ppm using the solvent peak at 2.49 ppm (DMSO-$d_6$) as an internal standard. 11.35 (s, 1H), 10.96 (s, 1H), 10.62 (s, 1H), 7.48 (dJ=1 Hz, 1H), 7.39 (d, J=10.0 Hz, 1H), 7.29 (d, J=10.0Hz, 1H), 7.14 (d, J=10 Hz, 1H), 7.07 (t, J=10.0 Hz, 1H), 6.99 (t, J=10.0 Hz, 1H), 6.93 (t, J=10.0 Hz, 1H), 6.88 (t, J=10.0 Hz, 1H), 5.26 (m, 1H), 3.30 (m, 2H) 1.64 (bs, 3H) and 1.61 ppm (bs, 3H). $^{13}C$ NMR spectra of compound II were recorded in $CDCl_3$ at 125 MHz on a Brucker DRX-500. Chemical shifts are given in ppm relative to TMS at zero ppm using the solvent peak at 77.0 ppm ($CDCl_3$) as an internal standard. 138.4, 138.3, 135.7, 135.2, 127.7, 121.6, 120.0, 119.8, 119.6, 110.7, 110.6, 100.5, 26.8, 25.8 and 18.0 ppm.

4.2.2 COMPOUND SYNTHESIS

EXAMPLE 1

2,5-Dihydroxy-3,6-di-[2-(2-methylbut-2-en-4-yl)indol-3-yl]1,4-quinone

A mixture of 100 mg. of 2,5-diacetoxy-3,6-dibromo-1,4-quinone, or other suitably protected quinone such as 3,6-dibromo-2,5-ditrimethylsiloxy-1,4-quinone, 3,6-dibromo-2,5-di-(t-butyldimethylsiloxy-1,4-quinone, 2,5-dibenzoxy-3,6-dibromo-1,4-quinone, 3,6-dibromo-2,5-diisobutryoxy-1,4-quinone, 2,5-dibenzyloxy-3,6-dibromo-1,4-quinone or 2,5-diallyoxycarbonyloxy-3,6-dibromo-1,4-quinone which can be prepared from commercially available 2,4-dibromo-3,6-dihydroxy-1,4-quinone and 180 mg of 3-[2-(2-methylbut-2-en-4-yl) indole, prepared by the Fisher indole synthesis, in 10 ml of anhydrous dimethylforamide, or pyridine or dimethylsulfoxide, with powdered potassium carbonate, was heated at 100° C. for 24 hours. The cooled mixture was partitioned between ethyl acetate and water. The ethyl acetate layer was then washed with brine, dried over sodium sulfate, filtered and concentrated. The crude was then purified on a medium pressure liquid chromatography column in a solvent mixture of dichloromethane and methanol to provide 25 mg of 2,5-diacetoxy-3,6-di-[2-(2-methylbut-2-en-4-yl) indol-3-yl]1,4-quinone. 2,5-Diacetoxy-3,6-di-[2(2-methylbut-2-en-4-yl)indol-3-yl]1,4-quinone was then hydrolysed with 1 N aqueous sodium hydroxide solution in methanol. Acidification of the above mixture produced the crude product after filtration. Further crystallization in ethanol and water produced the title compound. Other aforementioned protecting groups, they can be removed by conventional deprotection methods such as diluted acid, potassium fluoride or palladium (0) complex or palladium on carbon with hydrogen or by methods described by Greene and Wuts (Protective groups in organic synthesis, John Wiley and Son, 1991).

Alternatively, under the similar conditions, 2,3,5,6-tetrabromo-1,4-quinone reacts with excess indole in the presence of potassium carbonate and aluminum oxide in dimethylformamide or dimethylsulfoxide at 100° C. to produce the substituted 2,5-dibromo-3,6-(3-indolyl)-1,4-quinone which can react with base such as sodium hydroxide to give the substituted 2,5-dihydroxy-3,6-(3-indolyl)-1, 4-quinone (Hoerher, J.; Schwenner, E.; Franck, B., *Liebigs Ann. Chem.* 1986, 10: 1765–1771).

EXAMPLE 2

2,5-Diacetoxy-3,6-di-[2-(2-methylbut-2-en-4-yl)indol-3-yl] 1,4-quinone 2,5-Diacetoxy-3,6-di-[2-(2-methylbut-2-en-4-yl)indol-3-yl] 1,4-quinone was prepared in Example 1.

EXAMPLE 3
2,5-Diacetoxy-3,6-di-[2(3-methyl-n-butyl)indol-3-yl]1,4-quinone

Hydrogenation of 2,5-diacetoxy-3,6-di-[2-(2-methylbut-2-en-4-yl) indol-3-yl]1,4-quinone in methanol with 5% palladium on carbon under 1 atm of hydrogen produced the title compound.

EXAMPLE 4
2,5-Dihydroxy-3,6-di-[2-(3-methyl-n-butyl)indol-3-yl]1,4-quinone

Base hydrolysis of 2,5-diacetoxy-3,6-di-[2-(3-methyl-n-butyl)indol-3-yl]1,4-quinone as described in Example 1 produced the title compound.

Under similar conditions as those described in Examples 1 to 4, the following compounds are prepared using either 2,5-dibromo-3,6-dihydroxy-1,4-quinone or 2,3,5,6-tetrabromoquinone as starting materials:

EXAMPLE 5
3,6-Di-[5-(bromo)indol-3-yl]-2,5-dihydroxy-1,4-quinone

EXAMPLE 6
3,6-Di-[2-(allyl)indol-3-yl]-2,5-dihydroxy-1,4-quinone

EXAMPLE 7
2,5-Dihydroxy-3,6-di-[2-(n-propyl)indol-3-yl]1,4-quinone

EXAMPLE 8
3,6-Di-[2-(aminocarbonyl) indol-3-yl]-2,5-dihydroxy-1,4-quinone

EXAMPLE 9
2,5-Diacetoxy-3, 6-di-[2 (aminocarbonyl) indol-3-yl]-1,4-quinone

EXAMPLE 10
3,6-Di-[2-allylindol-3-yl]-2,5-dibenzoyloxy-1,4-quinone

EXAMPLE 11
2,5-Dihydroxy-3,6-di-[2-(cyano)indol-3-yl]1,4-quinone

EXAMPLE 12
2,5-Dihydroxy-3,6-di-[4-(methoxycarbonyl)indol-3-yl]1,4-quinone

EXAMPLE 13
2,5-Dihydroxy-3,6-di-[5,7-(dimethoxy)indol-3-yl]1,4-quinone

EXAMPLE 14
2,5-Dihydroxy-3,6-di-[4,7-(dimethoxy)indol-3-yl]1,4-quinone

EXAMPLE 15
2,5-Dihydroxy-3,6-di-[5-(nitro)indol-3-yl]1,4-quinone

EXAMPLE 16
3,6-di-[4(4-chlorobenzoylamino)indol-3-yl]-2,5-dihydroxy-1,4-quinone

EXAMPLE 17
3,6-di-[2-(4-chlorophenyl)indol-3-yl]-2,5-dihydroxy-1,4-quinone

EXAMPLE 18
2,5-Dihydroxy-3,6-di-[2-(4-fluorophenyl)indol-3-yl]1,4-quinone

EXAMPLE 19
2,5-Dihydroxy-3,6-di-[4,6-(dimethoxy)indol-3-yl]1,4-quinone

EXAMPLE 20
2,5-Dihydroxy-3,6-di-[2-(5-hydroxy-6-methoxy)indol-3-yl] 1,4-quinone

EXAMPLE 21
2,5-Dihydroxy-3,6-di-[4-(cyano)indol-3-yl]1,4-quinone

EXAMPLE 22
2,5-Dihydroxy-3,6-di-[5-(4-trifluoromethylphenylaminocarbonyl)indol-3-yl]1,4-quinone

EXAMPLE 23
2,5-Dihydroxy-3,6-di-[2-(4-trifluoromethylphenylaminocarbonyl)indol-3-yl]1,4-quinone

EXAMPLE 24
2,5-Dihydroxy-3,6-di-[2-(ethyl)indol-3-yl]1,4-quinone

EXAMPLE 25
3,6-di-[2-(5-bromo-6-nitro)indol-3-yl]-2,5-dihydroxy-1,4-quinone

EXAMPLE 26
2,5-Dimethoxy-3,6-di-[2-(2-methylbut-2-en-4-yl)indol-3-yl]1,4-quinone Methylation of Example 1 with methyl iodide and potassium carbonate in dimethylforamide followed by purification produced the title compound. This compound could also be prepared by heating 2,5-dibromo-3,6-di[2-(2-methylbut-2-en-4-yl)indol-3-y]1,4-quinone in methanol in the presence of powdered potassium carbonate.

EXAMPLE 27
2,5-Dimethoxy-3,6-di-[2(3-methyl-n-butyl)indol-3-yl]1,4-quinone

Hydrogenation of Example 26 under conditions as those in Example 3 produced the title compound.

EXAMPLE 28
Preparation of 2,5-Dihydroxy-3,6-di-[2-(3-methyl-n-butyl) indol-3-yl]-1,4-quinone To a glass tube containing 2-(3-methyl-n-butyl) indole (400 mg), bromanil (431 mg) and potassium carbonate (703 mg), equipped with a magnetic stir bar, was added dimethylformamide (10 ml). The mixture was stirred at room temperature for 40 h. Following dilution with 1 N HCl (100 ml), the crude mixture was extracted with ethyl acetate (200 ml) The organic layer was washed with brine (100 ml) and dried with sodium sulfate. After removal of solvent under reduced pressure, the crude residue was filtered through a short plug of flash silica, eluting with 30% ethyl acetate/hexane. The solvent was removed under reduced pressure, and the residue was purified by flash chromatography (15% ethyl acetate/hexane) to yield 2,5-dibromo-3,6-di-[2-(3-methyl-n-butyl) indol-3-yl]-1,4-quinone (40 mg, 7%) as a blue crystalline solid.

To a stirred solution of 2,5-dibromo-3,6-di-[2-(3-methyl-n-butyl) indol-3-yl]-1,4-quinone (40 mg) in methanol (1.5 ml) was added 2N methanolic sodium hydroxide (0.251 ml). The solution was stirred at room temperature for 24 h, followed by dilution with water (50 ml). The product was extracted with ethyl acetate (100 ml), washed with brine (50 ml) and dried with sodium sulfate. Removal of solvent under reduced pressure provided 2,5-methoxy-3,6-di-[2-(3-methyl-n-butyl) indol-3-yl]-1,4-quinone (30 mg, 90%) as a yellow crystalline solid.

To a stirred solution of 2,5-dimethoxy-3,6-di-[2-(3-methyl-n-butyl) indol-3-yl]-1,4-quinone (9 mg) in ethanol (2 ml) was added 1 N aqueous potassium hydroxide (1 ml). The mixture was heated at 85° C. for 3.5 h, then diluted with 1 N HCl (25 ml). The product was extracted with ethyl acetate (50 ml), washed with brine (25 ml) and dried with sodium sulfate. The solvent was removed under reduced pressure to afford 2,5-dihydroxy-3,6-di-[2-(3-methyl-n-butyl) indol-3-yl]-1,4-quinone (8 mg) as a reddish-brown crystalline solid.

28a) Preparation of 2-(2-methyl-1-buten-4-yl) indole To a stirred solution of 2-methylindole (1g) in diethylether (76 ml) under nitrogen was added a 1.6 M solution of n-butyllithium in hexane (14.3 ml) slowly dropwise via syringe. Potassium tert-butoxide (1.711 g) was then added, producing a bright yellow mixture. After stirring at room temperature under nitrogen for 50 min., the mixture was cooled to −78° C., whereupon 3-bromo-2-methylpropene (1.54 ml) was added dropwise via syringe, giving a red-orange solution. The reaction mixture was stirred at −78° C. for 2 h, then quenched with water (10 ml). After warming to room temperature, water (150 ml) and 1 N HCl (1 ml) was added to neutralize the reaction mixture. The mixture was extracted with ethyl acetate (250 ml), and the organic layer was washed with brine (100 ml) and dried with sodium sulfate. The solvent was removed under reduced pressure, and the crude residue was purified by flash chromatography (4-ethyl acetate/hexane) to afford 2-(2-methyl-1-butene-4-yl) indole (664 mg. 47%) as a waxy yellow solid.

28b) Preparation of 2-(3-methyl-n-butyl) indole Into a 3-necked round bottom flask under a blanket of nitrogen was placed 5% palladium catalyst on charcoal (771 mg). A solution of 2-(2-methyl-1-buten-4-yl) indole (671 mg) in ethanol (36 ml) was added to the flask, which was evacuated and charged with hydrogen twice. The mixture was stirred vigorously under hydrogen (1 atm) for 2 h, followed by filtration through a pad of Celite. The solvent was removed under reduced pressure and the crude residue was purified by flash chromatography (3% ethyl acetate/hexane) to give 2-(3-methyl-n-butyl) indole (400 mg, 59i) as a yellow crystalline solid.

EXAMPLE 29
Preparation of 2,5-Dihydroxy-3,6-di-[2-(methyl) indol-3-yl]-1,4-quinone Refer to Example 28 using 2-methylindole as the starting indole.

EXAMPLE 30
Preparation of 3,6-Di-(2-ethylindol-3-yl)-2,5-dihydroxy-1,4-quinone Refer to Example 28 using 2-ethylindole as the starting indole.

30a) Preparation of 2-ethylindole

Refer to 28a) using methyl iodide as the alkylating agent.

EXAMPLE 31
Preparation of 3,6-Di-(2-butylindol-3-yl) 2,5-dihydroxy-1,4-quinone Refer to Example 28 using 2-butylindole as the starting indole.

31a) Preparation of 2-(but-1-en-4- yl) indole

Refer to 28a) using allyl bromide as the alkylating agent.

31b) Preparation of 2-butylindole

Refer to 28b) using 2-(but-1-en-4-yl) indole as the starting material.

EXAMPLE 32
Preparation of 3,6-Di-[2-(but-1-en-4- yl) indol-3-yl] 2,5-dihydroxy-1,4-quinone Refer to Example 28 using 2-(but-1-e n-4-yl ) indole as the starting indole.

EXAMPLE 33
Preparation of 2,5-Dihydroxy-3,6-di-[2-(4-methyl-n-pentyl) indol-3-yl]-1,4-quinone Refer to Example 28 using 2-(4-methyl-n-pentyl) indole as the starting indole.

33a) Preparation of 2-(2-methyl-2-penten-5-yl) indole

Refer to 28a) using 4-bromo-2-methyl-2-butene as the alkylating reagent.

33b) Preparation of 2-(4-methyl-n-pentyl) indole

Refer to 28b) using 2-(2-methyl-2-penten-5-yl) indole as the starting material.

EXAMPLE 34
Preparation of 2,5-Dihydroxy-3,6-di-[2-(2-phenylethyl) indol-3-yl]-1,4-quinone Refer to Example 28 using 2-(2-phenylethyl) indole as the starting indole.

34a) Preparation of 2-(2-phenylethyl) indole

Refer to 28a) using benzyl bromide as the alkylating agent.

EXAMPLE 35
Preparation of 2,5-Dihydroxy-6-(indol-3-yl)-3-[2-(3-methyl-n-butyl) indol-3-yl]-1,4-quinone This synthesis could be achieved by treating 2-(3-methyl-n-butyl) indole with 2 equivalents of bromanil in the presence of potassium carbonate in dimethylformamide, followed by workup and purification similar to Example 28. The resultant mono-indolyl adduct could then be treated with 2 equivalents of indole under the same conditions as above to provide the bis-indolyl product.

EXAMPLE 36
Preparation of 3,6-Di-(5-carboxy-2-ethylindol-3-yl)-2,5-dihydroxy-1,4-quinone Refer to Example 28 using 5-carboxy-2-ethylindole as the starting indole.

36a) Preparation of 5-carboxy-2-ethylindole

This synthesis could start with 5-chloro-2-methylindole, which could be alkylated with methyl indole (see 28a). The product chloroindole could then be converted to its Grignard species and exposed to carbon dioxide to finish the synthesis.

EXAMPLE 37
Preparation of 3,6-Di-[5-carboxy-2-(n-propyl) indol-3-yl]-2,5-dihydroxy-1,4-quinone Refer to Example 28 using 5-carboxy-2-propylindole as the starting indole.

37a) Preparation of 5-carboxy-2-propylindole

Refer to 36a) using ethyl iodide as the alkylating agent.

EXAMPLE 38
Preparation of 3,6-Di-[5-carboxy-2-(3-methyl-n-butyl) indol-3-yl]-2,5-dihydroxy1,4-quinone Refer to Example 28 using 5-carboxy-2-(3-methyl-n-butyl) indole as the starting indole.

38a) Preparation of 5-carboxy-2-(2-methyl-1-buten-4-yl) indole

Refer to 36a) using 3-bromo-2-methylpropene as the alkylating agent.

38b) Preparation of 5-carboxy-2-(3-methyl-n-butyl) indole

Refer to 28b) using 5-carboxy-2-(2-methyl-1-buten-4-yl) indole as the starting material.

EXAMPLE 39

Preparation of 3,6-Di-[2-(4-carboxy-n-butyl) indol-3-yl]-2,5-dihydroxy-1,4-quinone Refer to Example 28 using 2-(4-carboxy-n-butyl) indole as the starting indole.

39a) Preparation of 2-(4-carboxy-3-buten-1-yl) indole

Refer to 28a) using 4-bromo-2-butenoic acid as the alkylating agent.

39b) Preparation of 2-(4-carboxy-n-butyl) indole

Refer to 28b) using 2-(4-carboxy-3-buten-1-yl) indole as the starting material.

EXAMPLE 40

Preparation of 3-[5-Carboxy-2-(3-methyl-n-butyl) indol-3-yl]-2,5-dihydroxy-6-(indol-3-yl)-1,4-quinone Refer to Example 35 using 5-carboxy-2-(3-methyl-n-butyl) indole in the first step.

EXAMPLE 41

Preparation of 3,6-Di-(5-amino-2-ethylindol-3-yl)-2,5-dihydroxy-1,4-quinone

Refer to Example 28 using 5-amino-2-ethylindole as the starting indole.

41a) Preparation of 5-amino-2-ethylindole This synthesis could be achieved beginning with a standard nitration of 2-ethylindole using sodium nitrate and sulfuric acid similar to that cited in Yokoyama; Tanaka; Yamane; Kurita; *Chem. Lett.*; 7; 1991; 1125–1128. The resultant 5-nitro-2-ethylindole could be reduced to the desired amino compound using catalytic hydrogenation as in 28b).

EXAMPLE 42

Preparation of 3,6-Di-[5-amino-2-(n-propyl) indol-3-yl]-2,5-dihydroxy-1,4-quinone Refer to Example 28 using 5-amino-2-(n-propyl) indole as the starting indole.

42a) Preparation of 5-amino-2-(n-propyl) indole

Refer to 41a) using 2-n-propylindole.

EXAMPLE 43

Preparation of 3,6-Di-[5-amino-2-(3-methyl-n-butyl) indol-3-yl] 2,5-dihydroxy-1,4-quinone Refer to Example 28 using 5-amino-2-(3-methyl-n-butyl) indole as the starting indole.

43a) Preparation of 5-amino-2-(3-methyl-n-butyl) indole

Refer to 41a) using 2-(3-methyl-n-butyl) indole.

EXAMPLE 44

Preparation of 2,5-Diacetoxy-3,6-di-[2-(3-methyl-n-butyl) indol-3-yl]-1,4-quinone This synthesis could be accomplished by treating 2,5-hydroxy-3,6-di-[2-(3-methyl-n-butyl) indol-3-yl]-1,4-quinone with acetic anhydride in the presence of pyridine.

EXAMPLE 45

Preparation of 3,6-Di-[2-ethyl-5-(4-ethylphenylsulfonylamino) indol-3-yl]-2,5-dihydroxy-1,4-quinone Refer to Example 28 using 2-ethyl-5-(4-ethylphenylsulfonylamino) indole as the starting indole.

45a) Preparation of 2-ethyl-5-(4-methylphenylsulfonylamino) indole

The above compound could be synthesized by treating 5-amino-2-ethylindole with p-toluenesulfonyl chloride in the presence of triethylamine.

EXAMPLE 46

Preparation of 2,5-Dihydroxy-3,6-di-[5-(4-methylphenylsulfonylamino)-2-(n-propyl) indol-3-yl]-1,4-quinone Refer to Example 28 using 5-(4-methylphenylsulfonylamino)-2-(n-propyl) indole as the starting indole.

46a) Preparation of 5-(4-methylphenylsulfonylamino)-2-(n-propyl) indole

Refer to 45a) using 5-amino-2-propylindole.

EXAMPLE 47

Preparation of 2,5-Dihydroxy-3,6-di-[2-(3-methyl-n-butyl)-5-(4-methylphenylsulfonylamino) indol-3-yl]-1,4-quinone Refer to Example 28 using 2-(3-methyl-n-butyl)-5-(4-methylphenylsulfonylamino) indole as the starting indole.

47a) Preparation of 2-(3-methyl-n-butyl)-5-(4-methylphenylsulfonylamino) indole

Refer to 45a) using 5-amino-2-(3-methyl-n-butyl) indole.

EXAMPLE 48

Preparation of 2,5-Dihydroxy-3,6-di-[2-(2-methylbut-1-en-4-yl) indol-3-yl]-1,4-quinone Refer to Example 28 using 2-(2-methylbut-1-en-4-yl) indole as the starting indole.

4.3 PROTEIN TYROSINE KINASE/ADAPTOR PROTEIN COMPLEXES

The PTK/adaptor protein complexes which may be disrupted by the methods and compositions of the invention comprise at least one member of the PTK family of proteins and at least one member of the adaptor family of proteins, as described below. Under standard physiological conditions, the components of such complexes are capable of forming stable, non-covalent attachments with one or more of the other PTK/adaptor protein complex components. Preferably, the compounds of the invention inhibit PTK/adaptor protein complexes wherein the PTK component is an epidermal growth factor receptor (EGF-R) protein tyrosine kinase molecule, a platelet derived growth factor receptor (PDGF-R) protein tyrosine kinase molecule or an insulin growth factor-like receptor tyrosine kinase molecule (IGF-1R).

Intracellular, cytoplasmic PTK components of the PTK/adaptor protein complexes may include, for example, members of the Src family, such molecules as src, yes, fgr, fyn, lyn, hck, lck, and blk; members of the Fes family, such as fes and fer; members of the Abl family, such as abl and arg; and members of the Jak family, such as jak1 and jak2. Transmembrane, receptor PTK components of the PTK/adaptor protein complexes may include, for example, such molecules as members of the FGF receptor, Sevenless/ROS, Insulin receptor, PDGF receptor, and EGF receptor family of growth factor receptors.

The adaptor protein components of the PTK/adaptor protein complexes comprise one or more SH2 and/or one or more SH3 non-catalytic domains. The SH2 and SH3 domains which may be a part of the adaptor proteins are as described, above, for the PTK components. Adaptor proteins which may be components of the PTK/adaptor protein complexes may include, for example, p85, c-Crk, SHC, Nck, ISGF3α, guanine triphosphatase activator protein (GAP), and members of the GRB subfamily of proteins, such as GRB1, GRB-2, GRB-3, GRB-4, GRB-7, and GRB-10.

4.4 TREATMENT OF PTK/ADAPTOR PROTEIN COMPLEX-RELATED CELL PROLIFERATIVE DISORDERS

The compounds and/or pharmaceutical compositions (described in Section 4.4.2, below) of the invention may be used for the treatment of cell proliferative disorders, such as oncogenic disorders, involving a PTK capable of complexing with a member of the SH2- and/or SH3-containing family of adaptor proteins. The compounds of the invention may be preferentially utilized in the treatment of cell proliferative disorders involving PTK/adaptor protein complexes wherein the PTK component is EGF-R, PDGF-R, MCT or IGF-1R.

Among the oncogenic disorders which may be treated by the compounds of the invention are, for example, BCR-ABL-associated cancers (such as, for example, chronic myelogenous and acute lymphocytic leukemias), gliomas, glioblastomas, melanoma, human ovarian cancers, human breast cancers (especially HER-2/GRB-7-associated human breast cancers), and human prostate cancers.

Assays for determining the effectiveness of a compound in the disruption of a PTK/adaptor protein complex are described, below, in Section 4.4.1. Methods for the administering the compounds and/or pharmaceutical compositions of the invention to patients are described, below, in Section 4.4.2.

"Disruption", as used here, is meant to refer not only to a physical separation of PTK/adaptor protein complex components, but is also meant to refer to a perturbation of the activity of the PTK/adaptor complexes, regardless of whether or not such complexes remain able, physically, to form. "Activity", as used here, refers to the function of the PTK/adaptor protein complex in the signal transduction cascade of the cell in which such a complex is formed, i.e., refers to the function of the complex in effecting or inhibiting the transduction of an extracellular signal into a cell. The compounds and pharmaceutical compositions of the invention do not, however, directly interfere with (i.e., inhibit or enhance) the enzymatic activity of the protein tyrosine kinase of interest. 4.4.1 ASSAYS FOR THE DISRUPTION OF PTK/ADAPTOR PROTEIN COMPLEXES A variety of methods may be used to assay the ability that the compounds of the invention exhibit to disrupt PTK/adaptor protein complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound.

Additionally, in vivo complex formation may be assayed by utilizing co-immunoprecipitation techniques well known to those of skill in the art. Briefly, a cell line capable of forming a PTK/adaptor complex of interest may be exposed to one or more of the compounds of the invention, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

The effect of a compound of the invention on the transformation capability of the PTK/adaptor protein of interest may be directly assayed. For example, one or more of the compounds of the invention may be administered to a cell such as a fibroblast or hematopoietic cell capable of forming a PTK/adaptor complex which, in the absence of a compound of the invention, would lead to the cell's transformation (Muller, A. J. et al., 1991, Mol. Cell. Biol. 11:1785–1792; McLaughlin, J. et al., 1987, Proc. Natl. Acad. Sci. USA 84:6558–6562). The transformation state of the cell may then be measured in vitro, by monitoring, for example, its ability to form colonies in soft agar (Lugo and Witte, 1989, Mol. Cell. Biol. 9:1263–1270; Gishizky, M. L. and Witte, O. N., 1992, Science 256:836–839). Alternatively, a cell's transformation state may be monitored in vivo by determining its ability to form tumors in immunodeficient nude or severe combined immunodeficiency (SCID) mice (Sawyers, C. L. et al., 1992, Blood 79:2089–2098). Further, the ability of the compounds of the present invention, to inhibit various tumor cell lines, such as for example, melanoma, prostate, lung and mammary tumor cell lines established as SC xenografts can be examined.

4.4.2 PHARMACEUTICAL COMPOSITIONS AND METHODS OF ADMINISTRATION

The compounds of the invention, as described, above, in Section 5.1, may be administered to a patient at therapeutically effective doses to treat or ameliorate cell proliferative disorders involving PTK/adaptor protein interactions. A therapeutically effective dose refers to that amount of the compound sufficient to result in amelioration of symptoms of a cell proliferative disorder.

Described, below, in Section 5.4.2.1, are methods for determining the effective dosage of the compounds of the invention for the treatment of cell proliferative disorders. Further, described, below, in Section 5.4.2.2, are methods for formulations and pharmaceutical compositions comprising the compounds of the invention, and methods for the administration of such compounds, formulations, and compositions.

4.4.2.1 EFFECTIVE DOSE

Toxicity and therapeutic efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Dosage amount and interval may be adjusted individually to provide plasma levels of the active moiety which are sufficient to maintain inhibition of adaptor protein/protein tyrosine kinase interactions, or minimal effective concentration (MEC). The MEC will vary for each compound but can be estimated from in vitro data, e.g., the interactions using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

4.4.2.2 FORMULATIONS AND ADMINISTRATION

As discussed, above, adaptor proteins are intracellular proteins. Thus, PTK/adaptor protein interactions are intracellular, regardless of whether the PTK of interest is of the transmembrane or the intracellular type. Therefore, the compounds of the invention act intracellularly to interfere with the formation and/or activity of the PTK/adaptor complexes. A variety of methods are known to those of skill in the art for administration of compounds which act intracellularly, as, for example, discussed in this Section.

Pharmaceutical compositions for use in accordance with the compounds of the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5. EXAMPLE: THE COMPOUNDS INHIBIT EGF-RECEPTOR/GRB-2 SH2 DOMAIN INTERACTION

In the Example presented in this Section, Compound I is demonstrated to effectively inhibit the binding of tyrosine phosphorylated EGF-receptor to a GRB-2 SH2 peptide domain.

5.1 MATERIALS AND METHODS

Adaptor-GST Fusion Protein

The adaptor-GST (glutathione-S-transferase) fusion proteins used herein were GRB-2-GST fusion proteins prepared by expression in *E. coli* transformed with GRB-2/pGEX constructs. The GRB-2 portions of these fusion proteins consisted of only the SH2 domain of the GRB-2 protein. Transformed cells are grown in Luria broth (LB) supplemented with ampicillin. After reaching an optical density (OD) at 600 nm of 0.3, the cells are induced for 6 hours with isopropyl β-D-thiogalactopyranoside (IPTG) in order to express the fusion protein.

After the 6 hour expression period, the cells are precipitated, pelleted at 10,000×g for 10 minutes at 4° C., washed, and resuspended in phosphate buffered saline (PBS). Next, the cells are lysed by sonication (6 strokes, 5 seconds per stroke). Insoluble material is removed by centrifugation at 10,000×g for 10 minutes at 4° C., and the supernatant is passed over a Glutathion-Sepharose column. Bound GRB-2-GST fusion protein is eluted off the column with 5 mM reduced glutathion, then dialyzed against PBS.

Immobilized EGF-R Tyrosine Kinase Molecule

Epidermal growth factor receptor tyrosine kinase (EGF-R). EGF-R was isolated from cells overexpressing EGF-R, specifically, the A431 (ATCC CRL 1551), cell line. The cells are lysed in HNTG buffer (20 mM Hepes/HCl, pH 7.4, 150 mM NaCl, 1.0% Triton X-100, 5% glycerol, 1 mM phenyl-methylsulfonyl fluoride (PMSF), 1 mg/L aprotonin, 1 mg/L leupeptin, 10 mg/L benzamidine).

EGF-R protein was isolated from the cell lysates by immobilization onto microtiter plates, as described below. EGF-R was subsequently phosphorylated in vitro, as explained below.

The EGF-R molecule was immobilized onto microtiter plates. Microtiter plates were prepared by first coating the wells of the plate, overnight at 4° C., with an anti-EGF-R monoclonal antibody directed against the extracellular domain of EGFR (UBI, #05-101) at a concentration of 0.5 μg (in PBS) per microtiter well, at a final volume of 150 μl per well.

After overnight coating, the coating solution was removed from the microtiter wells, and replaced with blocking buffer (5% dry milk in PBS) for 30 minutes at room temperature, after which the blocking buffer is removed and the wells were washed 4 times with TBST buffer (150 mM NaCl, 50 mM Tris-HCl, pH 7.2, 0.1% Triton X-100).

Cell lysate from EGF-R-expressing cells were added to each well, in 150 μl of PBS, incubated 30 minutes at room temperature, with shaking. Unbound EGF-R was removed by washing wells 5 times with TBST buffer. Approximately 50–100 ng of EGF-R protein was bound per well.

It was important to use an EGF-R overexpressing cell line which exhibits a high endogenous phosphatase activity, such as the A431 cell line used herein. This is because during lysis and incubation with the immobilized antibody, the phosphatases remove phosphate groups from the EGF-R molecules, thus prohibiting endogenous adaptor proteins, such as GRB proteins, to bind EGFR, which could potentially lead to artifactual results. Alternatively, cells may be starved before lysis, if the cell line utilized may be readily starved.

Preparation of Autophophorylated EGF-R

The following in vitro kinase reaction yielded autophosphorylated EGF-R. The kinase reaction was initiated by the addition of 15 μl of ATP/$Mn^{2+}$ mix (in 50 mM $MnCl_2$, final concentration of 10 μM ATP, for a total volume of 150 μl. The plate was incubated for 5 minutes at room temperature, shaking, the supernatant was aspirated, and the plates were then washed 5 times with TBST.

Assay Procedure

Either 30 ng GRB-2-GST fusion proteins (i.e. a 1:1 ratio of EGF-R:GRB-2 proteins) or 5 ng GRB-2-GST fusion proteins (i.e. a 4:1 ratio of EGF-R:GRB-2 proteins) were added to the phosphorylated EGF-R coated microtiter wells in incubation buffer (0.1 M potassium phosphate buffer, pH 6.5) for 30 minutes, at room temperature, in the presence of Compound I. Control wells were incubated with GRB-2-GST fusion proteins in the absence of Compound I.

After incubation, wells were washed extensively with TBST. The amount of GRB-2-GST fusion protein bound to the immobilized EGF-R is then preferably determined with a purified rabbit antiserum against the GST-moiety of the fusion protein (AMRAD, New Victoria, Australia; Catalog No. 00001605). Incubations were for 30 minutes at room temperature. After incubation, antibody was removed and the wells are washed extensively with TBST. For visualization, wells were next incubated with a TAGO goat-anti-rabbit peroxidase antibody at room temperature for 30 minutes. After incubation, the antibody was removed, the wells were washed with tap water, and then with TBST. Substrate solution, ABTS (2,2'-Azinobis(3-ethylbenzthiazolinesulfonic acid)/$H_2O_2$ (1.2 μl $H_2O_2$ to 10 ml ABTS) was applied to the wells, and incubated for 20 minutes at room temperature. The reaction was stopped by addition of $5NH_2SO_4$. The O.D. at 410 nm was determined for each well. Utilizing this technique, it is normally possible to detect as little as 2 ng GRB-2-GST over background.

Alternatively, after incubation of the test substance and the GRB-2-GST fusion protein on the EGF-R wells, biotinylated monoclonal antibodies e.r., EL-6 or EL-12, may be utilized to assay fusion protein binding. The epitopes recognized by such antibodies map on the SH2 domain of GRB-2, but do not interfere with GRB-2 binding to phosphorylated EGFR. Binding of these antibodies is then determined by using a streptavidin-biotinylated horseradish peroxidase reactant.

Additionally, after incubation of the test substance and the GRB-2-GST fusion protein on the EGF-R wells, binding of the fusion protein to the immobilized EGFR may be assayed by incubating with 1 mM 1-chloro-2,4 dinitrobenzene (CDNB) and 1.54 mg/ml reduced glutathion in incubation buffer. The OD is then measured at 340 nm. This reaction is linear up to OD 1.0, and can be stopped with competitive GST inhibitors, as described in Mannervik and Danielson (Mannervik, B. and Danielson, U. H., 1988, CRC Critical Reviews in Biochemistry 23:238).

5.2 RESULTS

Compound I was tested for its ability to inhibit the binding of tyrosine phosphorylated EGF-receptor to an SH2 peptide domain of the GRB-2 adaptor protein, according to the assays described, above, in Section 5.1.

Compound I proves to be a potent inhibitor of GRB-2/SH2 binding, having an $IC_{50}$ of 2.9 μM. ($IC_{50}$, as used herein, return to the concentration of test compound required to inhibit one-half of GRB-2/SH2 binding relative to the amount of binding which occurs in the absence of test compound.)

6. COMPOUND I INHIBITS bcr/abl ACTIVITY

The Example presented herein demonstrates that compounds of the invention inhibits cell survival bcr/abl-transformed cell line.

6.1 MATERIALS AND METHODS (1) Cell lines used in this assay are: 32D cl.3: murine lymphoblastoid cell, IL-3 dependent.
   32D cl.3 J2/leuk: 32D cl.3 expressing raf and myc, IL-3 independent.
   32D bcr/abl: 32D over expressing bcr/abl kinase, pooled, IL-3 independent.
(2) All the above cell lines were grown in incubator with 5% $CO_2$ and 37° C. Their growth media are: 32D cl.3: RPMl+10% FBS+1 ng/ml IL-3+2 mM Glutamine.
   32D cl.3 J2/leuk: RPMl+10% FBS+2 mM Glutamine.
   32D bcr/abl: RPMl+10% FBS+2 mM Glutamine.
   IL-3: Interleukin-3, mouse (UBI Cat. #01-374)
(3) PBS (Dulbecco's Phosphate Buffered Saline) Gibco Cat. #450-1300EB
(4) MTT (3-[4,5-Dimethylthiazol-2-yl]-2,5-diphenyltetrazolium bromide; Thiazolyl blue) Sigma Cat. #M-2128
   working solution: 5 mg/ml PBS, store in dark @ 4° C.

(5) Solubilization Buffer
SDS Electrophoresis Grade, Fisher Cat. #BP 166.
N,N-Dimethyl-formamide (DMF), Fisher Cat. #BP1160.
Acetic Acid, Glacial, Fisher Cat. #A38.
working solution: Dissolve 200 g SDS in 250 ml warm $H_2O$ and 500 ml DMF, stir in low heat. When SDS is almost solubilized, add 25 ml 80% acetic acid and 25 ml 1N HCL to solution. Adjust volume to 1000 ml.

6.2 PROCEDURE

All of the following steps were conducted at room temperature unless specifically indicated.

6.2.1 CELL SEEDING (1) The cells were grown in tissue culture dish (10 cm, Corning 25020-100) to about $1 \times 10^6$ cell/ml, subculture every 2–3 days at 1:10 (1:20 for 32D bcr/abl line).

(2) Viable cells were counted with trypan blue according to standard procedure.

(3) Cells were then resuspended in fresh medium at a density of $2 \times 10^5$ cells/ml, and transfer cells to 96-well tissue culture plate (Corning, 25806-96) at 50 μl per well to reach about $2 \times 10^4$ cells/well. Each cell line was plated with its own positive and negative control: (negative control:medium alone).

32D c1.3 seeding medium should contain 2 ng/ml IL-3.

6.2.2 ASSAY PROCEDURES (1) Compound I drug stock (10 mM in DMSO) was diluted 1:50. 1:2 serial dilutions were performed for the remaining 8 wells in each line of the tissue culture plate. 50 μl were added to each well. Control wells received medium alone. Cells were incubated with drugs in 5% $CO_2$ at 37° for 15 hrs.

(2) 15 μl MTT were added to each well. Plates were incubated at 37° C. for 4 hours.

(3) After 4 hours, 100 μl solubilization solution was added to each well.

(4) Plates were covered with Aluminum foil, and allowed to sit on an ELISA plate shaker and shake overnight at room temperature to completely solubilize formazan crystals.

(5) Absorbance was read at 570 nm wavelength with a reference wavelength of 630 nm using a Dynatech ELISA plate reader, Model MR 500.

6.3 RESULTS

Compound I was tested herein for its ability to affect bcr/abl activity, and was found to be an inhibitor of bcr/abl function.

The effect of Compound I on bcr/abl function was tested using the cell growth assay described, above, in Section 6.1. Briefly, three cell lines were used in this assay. First, an IL-3 dependent cell line (32D c1.3) was used, which requires the presence of the IL-3 cytokine for survival. Next, two IL-3 independent cell lines were used, including 32D c1.3 J2/leuk, which consists of the 32D c1.3 cell line transformed with raf and myc, and 32D bcr/abl, which consists of the 32D c1.3 cell line transformed with bcr/abl. Because these latter cell lines are made IL-3 independent due to the activity of the products produced by the gene sequences they have been transformed by, if these products become inactive and the cells are not exposed to IL-3, the cell will not survive. Thus, for example, if bcr/abl is inactivated in the 32D c1.3 bcr/abl cell line, cells will be unable to survive in the absence of IL-3.

Compound I inhibits the ability of the 32D c1.3 bcr/abl cell line to survive in the absence of IL-3. This result is significant as this cell line is quite robust.

7. EXAMPLE: COMPOUND I INHIBITS CELLULAR PROLIFERATION

The Example presented herein demonstrates that Compound I of the invention is a potent inhibitor of cellular proliferation.

7.1 MATERIALS AND METHODS

Sulforhodamine B (SRB) Growth Assays

Assay 1: MCF-7SRB Growth Assay.

MCF-7 (ATCC# HTB 22) cells (H+B22) were seeded at 2000 cells/well in a 96-well flat bottom plate in normal growth media, which was 10% FBS/RPMI supplemented with 2 mM Glutamine. The plate of cells was incubated for about 24 hours at 37° C. after which it received an equal volume of compound dilution per well making the total volume per well 200 μl. The compound was prepared at 2 times the desired highest final concentration and serially diluted in the normal growth media in a 96-well round bottom plate and then transferred to plate of cells. DMSO serves as the vector control up to 0.2% as final concentration. The cells were then incubated at 37° C. in a humidified 5% $CO_2$ incubator. Four days following dosing of compound, the media was discarded and 200 μl/well of ice-cold 10% TCA (Trichloroacetic Acid) was added to fix cells. After 60 minutes at 4° C., the TCA was discarded and the plate was rinsed 5 times with water. The plate was then air-dried and 100 μl/well of 0.4% SRB (Sulforhodamine B from Sigma) 20 in 1% Acetic Acid was added to stain cells for 10 minutes at room temperature. The SRB was discarded and the plate was rinsed 5 times with 1% Acetic Acid. After the plate was completely dried, 100 μl/well of 10 mM Tris-base was added to solubilize the dye. After 5 to 10 minutes, the plate was read on a Dynatech ELISA Plate Reader at dual wavelengths at 570 nm and 630 nm.

Assay 2: PDGF-R/SRB Adherent Cells Growth Assay.

Compounds were tested for inhibition of anchorage-dependent tumor cell growth using the calorimetric assay described by Skehan et al., 1990. *J. Natl. Cancer Inst.* 82:1107–1112. The assay measures protein content of acid-fixed cells using the counterion binding dye sulforhodamine B (SRB, Sigma). The compounds were solubilized in DMSO (Sigma, cell culture grade) and diluted into appropriate growth medium at two-fold the desired final assay concentration. In assays using C6 cells (CCL 107), compounds (100 μl) were added to 96-well plates containing attached cellular monolayers (2000 cells/well in 100 μl). C6 (ATCC# CCL 107) cells were maintained in Ham's F10 supplemented with 5% fetal bovine serum (FBS) and 2 mM glutamine (GLN). After 4 days (37° C., 5% $CO_2$) the monolayers were washed 3 times with PBS and fixed with 200 μl ice-cold 10% TCA (Fisher Scientific), and kept at 4° C. for 60 min. The TCA was removed and the fixed monolayers were washed 5 times with tap water and allowed to dry completely at room temperature on absorbent paper. The cellular protein was stained for 10 min with 100 μl 0.4% SRB dissolved in 1% acetic acid. After 5 washes with tap water, the dye was solubilized in 10 mM Tris base (100 μl per well) and absorbance read at 570 nm on a Dynatech plate reader model MR5000. Growth inhibition data were expressed as a percentage of absorbance detected in control wells which were treated with 0.40 DMSO alone. DMSO controls were not different from cells grown in regular growth medium. $IC_{50}$ values were determined using a four parameter curve fit function.

For the anchorage-independent tumor cell growth assay, cells (3000 to 5000 per dish) suspended in 0.4% agarose in assay medium (DMEM containing 10% FCS) with and without Compounds were plated into 35 mm dishes coated with a solidified agarose base layer (0.8% agarose). After a 2 to 3 week incubation at 37° C., colonies larger than 50 μm were quantified using an Omnicon 3800 Tumor Colony counter.

Assay 3: MCF-7/HER-2B Growth Assay.

The protocol used herein is essentially similar to that described above (for the MCF-7 Growth Assay) except that immediately before Compound I was added, the normal growth media was removed and 0.5% FBS/RPMI supplemented with 2 mM Glutamine is added onto the cells. The compound was also prepared in this 0.5% serum media. The plate of cells was incubated for four days and developed as per standard techniques.

Assay 4: A431/SRB Growth Assay. A431 (ATCC# CRL 1555) cells were tested essentially according to the protocol described, above, for the MCF-7/HER-2B growth assay.

7.2 RESULTS

A number of cell lines were contacted to Compound I to test Compound I's effects on cell proliferation, utilizing the SRB protocols described, above, in Section 7.1.

As shown below, Compound I proved to be a potent inhibitor of cells proliferation of each of the four cell lines tested.

| Cell Line | Compound I $IC_{50}$ (MM) |
|---|---|
| C6 | 8 |
| A431 | 7.5 |
| MCF7 | 10 |
| MCF7-HER 2 | 6 |

$IC_{50}$, as used herein, refers to the concentration of test compound required to inhibit cell proliferation to 50% of the level seen in the same cell line which has not been contacted to test compound (in this case, Compound I).

Thus, the results depicted in this Section demonstrate that Compound I acts to inhibit cell proliferation. These results, taken together with those shown in the Example presented in Section 5, above, which demonstrated that Compound I acts to inhibit adaptor protein binding to the SH2 domain of the protein tyrosine kinase receptor EGFR, indicate that Compound I acts as a cell growth inhibitor that acts by blocking adaptor protein interaction with its binding partners (such as, for example, protein tyrosine kinase molecules). Given this Compound I activity, the compound may represent an anti-cell proliferation agent.

8. EXAMPLE: 3T3 CELLULAR PROLIFERATION INHIBITION ASSAY

The following protocol describes the procedures used to determine the ability of the compounds to inhibit cellular proliferation in 3T3 engineered cell lines that over expressing EGFr, IGF1r, or PDGFr.

8.1 MATERIALS AND REAGENTS (1) EGF Ligand: stock concentration=16.5 $\mu$M; EGF 201, TOYOBO, Co., Ltd. Japan.

(2) IGF1 Ligand: human, recombinant; G511, Promega Corp, USA.

(3) PDGF Ligand: human PDGF B/B; 1276-956, Boehringer Mannheim, Germany.

(4) SRB: sulfohodamine B; S-9012, Sigma Chemical Co., USA.

SRB Dye Solution: 0.4% SRB in 1% acetic acid, glacial.

(5) Acetic Acid, Glacial: A38-212, Fisher Scientific, USA.

(6) Albumin, Bovine: fraction V powder; A-8551, Sigma Chemical Co., USA.

(7) TCA Buffer: 100i trichloroacetic acid (A32-500, Fisher Scientific, USA).

(8) Tris Base Buffer: 10 mM tris base (BP152-5, Fisher Scientific, USA).

8.2 PROCEDURE (1) N-1H 3T3 (ATCC# 1658) engineered cell liens: 3T3-EGFr, 3T3-IGF1r, 3T3-PDGFr.

(2) Cells are seeded at 8000 cells/well in 10% FBS+2mM GLN DMEM, in a 96 well plate. Cells are incubated at 37° C. 5% $CO_2$ for overnight to allow the cells attach plate.

(3) On day 2, the cells are quiesced in the serum free medium (0% FBS DMEM) for 24 hours.

(4) On day 3, the cells are treated with the ligands (EGF=5 nM, IGF1=20 nM, or PDGF=100 ng/ml) and drugs at the same time. The ligands are prepared in the serum free DMEM with 0.1% bovine albumin. The negative control cells receive the serum free DMEM with 0.1% bovine albumin only; the positive control cells receive the ligands (EGF, IGF1, or PDGF) but no drugs. The drugs are prepared in the serum free DMEM in a 96 well plate, and a serial dilution is taken the place. A total of 1 $\mu$l/well medium of the diluted drugs are added into the cells. The total volume of each well is 200 $\mu$L. Quadruplicates (wells) and 11 concentration points are applied to each drug tested.

(5) On day 4, adding the ligands (EGF, IGF1, or PDGF) to the cells again, and to keep the final ligand concentration in the cells as same as previous.

(6) On day 5, the cells were washed with PBS and fixed with 200 $\mu$l/well ice cold 10% TCA for 1 hour under 0–5° C. condition.

(7) Remove TCA and rinse wells 5 times with de-ionized water. Dry plates upside down with paper towels. Stain cells with 0.4% SRB at 100 $\mu$L/well for 10 minutes.

(8) Pour off SRB and rinse plate 5 times with 1% acetic acid. Dry plate completely.

(9) Solubilize the dye with 10 mM Tris-base at 100 $\mu$L/well for 10 minutes on a shaker.

(10) Read the plate at dual wavelengths at 570 nm and 630 nm on Dynatech Elsia plate reader.

8.3 ASSAY PROCEDURES (1) Dilute drug stock (10 mM in DMSO) 1:50 in RPMI medium in first well, then do 1:2 dilution for 8-points in tissue culture plate. Transfer 50 $\mu$l/well of this solution to the cells. Control wells receive medium alone. Incubate the cells with drugs in 5% $CO_2$ at 37° for 15 hrs.

(2) Add 15 $\mu$l MTT to each well. Incubate plate at 37° C. for 4 hours.

(3) After 4 hours, add 100 $\mu$l solubilization solution to each well.

(4) Cover the plate with Aluminum foil, let plate sit on ELISA plate shaker and shake overnight at room temperature to completely solubilize formazan crystals.

(5) Read absorbance at 570 nm wavelength with a reference wavelength of 630 nm using a Dynatech ELISA plate reader, Model MR 500.

It is apparent that many modifications and variations of this invention as set forth here may be made without departing from the spirit and scope thereof. The specific embodiments described hereinabove are given by way of example only and the invention is limited only by the terms of the appended claims.

What is claimed is:

1. A method of inhibiting protein tyrosine kinase polypeptide/adaptor polypeptide interactions in a cell which comprises contacting the cell with a 2,5-bisindol-3-yl-1,4-quinone compound.

2. The method of claim 1 wherein the cell is in an animal.

3. The method of claim 2 wherein the animal is a mammal.

4. The method of claim 3 wherein the mammal is a human.

5. The method of claim 1 wherein the contact is achieved by in vivo administration.

6. The method of claim 5 wherein said administration is parental, oral, buccal, rectal, by inhalation or by insufflation.

7. The method of claim 1 wherein the inhibiting of the protein tyrosine kinase polypeptide/adapter polypeptide interactions results in amelioration of symptoms of a cell proliferative disorder.

8. A method of ameliorating the symptoms of a cell proliferative disorder wherein the cell proliferative disorder involves a protein tyrosine kinase polypeptide/adapter polypeptide complex which comprises administering an effective amount of a 2,5-bisindol-3-yl-1,4-quinone compound, and a pharmaceutically acceptable carrier.

9. The method of claim 8 wherein the cell proliferative disorder occurs in a mammal and the compound contacts the cell within a mammal so that the symptoms of the cell proliferative disorder in the mammal are ameliorated.

10. The method of claim 8 wherein the cell proliferative disorder is a BCR-ABL-associated cancer, a glioma, a glioblastoma, a melanoma, an ovarian cancer, a breast cancer, or a prostate cancer.

11. The method of claim 10 wherein the BCR-ABL-associated cancer is selected from the group consisting of chronic myelogenous leukemia and acute lymphocytic leukemia.

12. The method of claim 10 wherein the breast cancer is a HER-2/GRB-7- associated human breast cancer.

13. The method of claim 1 wherein the 2,5-bisindol-3-yl-1,4-quinone compound is a compound of the formula:

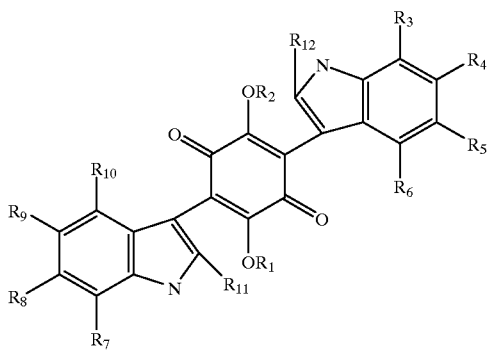

or a pharmaceutically acceptable salt thereof, wherein:

$R_1$ and $R_2$ are each independently hydrogen, lower alkyl, acetyl, aryl, alkylaryl or higher alkyl acid ester, and wherein at least one of $R_1$ and $R_2$ is other than hydrogen; and $R_3$ to $R_{12}$ are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, mercapto or 2-methylbut-2-en-4-yl; and wherein at least one of $R_{11}$ and $R_{12}$ is 2-methylbut-2-en-4-yl.

14. The method of claim 1 wherein the 2,5-bisindol-3-yl-1,4-quinone compound is a compound of the formula:

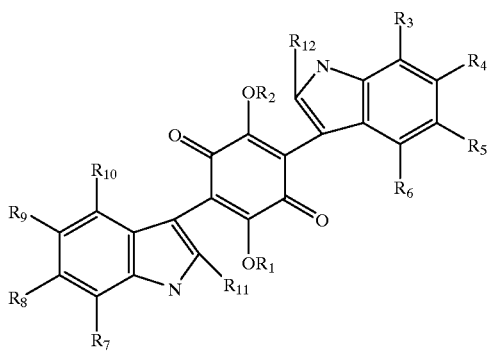

or a pharmaceutically acceptable salt thereof, wherein:

$R_1$ and $R_2$ are both H;

$R_3$ to $R_{10}$ are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, mercapto or 2-methylbut-2-en-4-yl; and $R_{11}$ and $R_{12}$ are each independently H or 2-methylbut-2-en-4-yl, wherein at least one of $R_{11}$ and $R_{12}$ is 2-methylbut-2-en-4-yl;

wherein at least one of $R_3$ to $R_{10}$ is other than H.

15. The method of claim 1 wherein the 2,5-bisindol-3-yl-1,4-quinone compound is a compound of the formula:

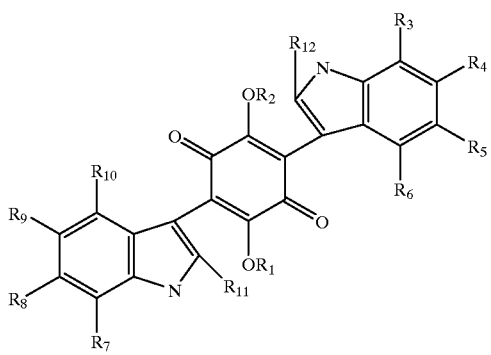

or a pharmaceutically acceptable salt thereof, wherein:

$R_1$ and $R_2$ are each independently aryl, alkylaryl and higher alkyl acid ester; and $R_3$ to $R_{12}$ are each independently H, alkyl, alkylcarboxy, alkenyl, alkenylcarboxy, aryl, alkylaryl, OH, alkoxy, nitro, fluoro, chloro, iodo, trihalomethyl, amide, carboxamide, carboxy, sulfonyl, sulfonamide, amino, or mercapto.

16. The method of claim 1 wherein the 2,5-bisindol-3-yl-1,4-quinone compound is a compound of the formula:

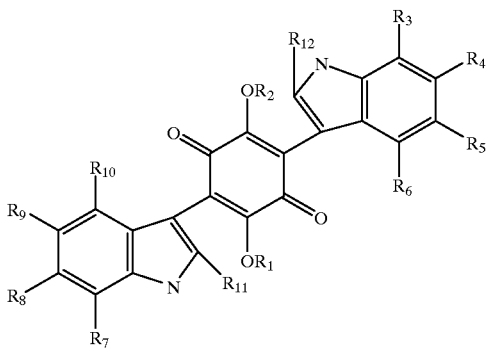

or a pharmaceutically acceptable salt thereof, wherein:

$R_1$, $R_2$, $R_{11}$ and $R_{12}$ are H; and $R_3$ to $R_{10}$ are each independently H, alkyl, alkylcarboxy, alkenyl, alkenylcarboxy, aryl, alkylaryl, alkoxy, hydroxy, nitro, halo, trihalomethyl, amide, carboxamide, carboxy, sulfonyl, sulfonamide, amino, or mercapto, wherein at least one of $R_3$ to $R_{10}$ is other than H, wherein:

(a) when $R_4$–$R_{10}$ are each H, $R_3$ may not be 2-methylbut-2-en-4-yl or 2-hydroxy-2-methylbut-4-yl; and (b) when $R_4$–$R6$ and $R_8$–$R_{10}$ are each H, $R_3$ and $R_7$ may not simultaneously be 2-methylbut-2-en-4-yl; and (c) when $R_3$–$R_4$, $R_6$–$R_8$ and $R_{10}$ are H, $R_5$ and $R_9$ may not simultaneously be 2-methylbut-2-en-4-yl or 3-methyl-n-butyl; and (d) when $R_3$, $R_5$–$R_7$, $R_9$–$R_{10}$ are H and $R_4$ and $R_8$ may not both be 2-methylbut-2-en-4-yl or 2-methylbut-1,3-dien-4-yl, and $R_4$ and $R_8$ may not be 2-methylbut-2-en-4-yl and 2-methylbut-1,3-dien-4-yl.

17. The method of claim 16 wherein the 2,5-bisindol-3-yl-1,4-quinone compound is a compound of the formula:

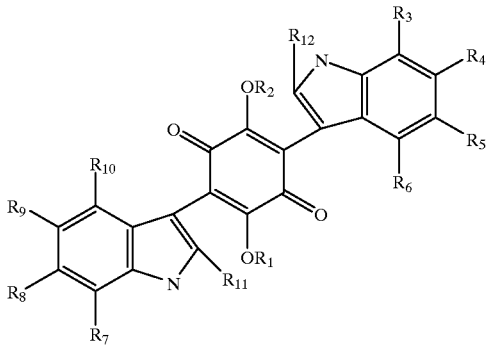

wherein $R_3$–$R_5$ and $R_7$–$R_9$ are H and either or both of $R_6$ and $R_{10}$ are 2-methylbut-2-en-4-yl.

18. The method of claim 1 wherein the 2,5-bisindol-3-yl-1,4-quinone compound is a compound of the formula:

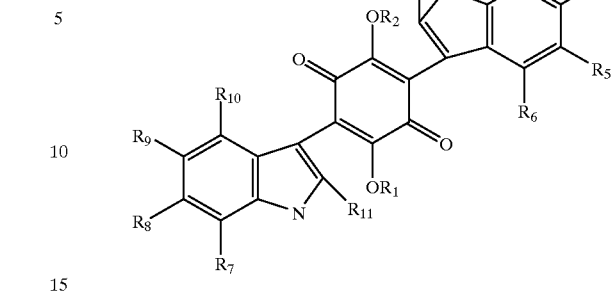

or a pharmaceutically acceptable salt thereof, wherein:

at least one of $R_1$ and $R_2$ is acetyl;

$R_{11}$ and $R_{12}$ are H; and $R_3$ to $R_{10}$ are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, and mercapto, wherein:

(a) when both $R_1$ and $R_2$ are acetyl; or when one of $R_1$ and $R_2$ is acetyl and $R_3$–$R_4$, $R_6$–$R_8$ and $R_{10}$–$R_{12}$ are H; $R_5$ and $R_9$ may not simultaneously be 2-methylbut-2-en-4-yl;

(b) when both $R_1$ and $R_2$ are acetyl and when $R_4$–R6 and $R_8$–$R_{10}$ are H, $R_3$ and $R_7$ may not simultaneously be 2-methylbut-2-en-4-yl;

(c) when both $R_1$ and $R_2$ are acetyl and when $R_3$, $R_5$–$R_7$, and $R_9$–$R_{10}$ are H, $R_4$ and $R_8$ may not simultaneously be 2-methylbut-2-en-4-yl.

19. The method of claim 1 wherein the 2,5-bisindol-3-yl-1,4-quinone compound is a compound of the formula:

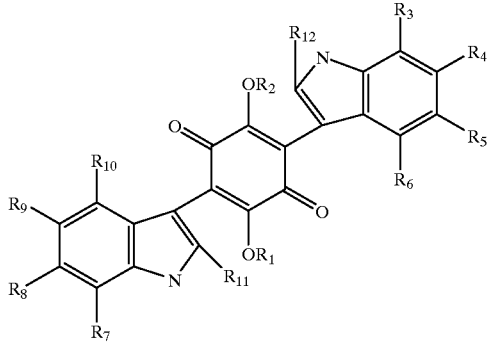

or a pharmaceutically acceptable salt thereof, wherein:

at least one of $R_1$ and $R_2$ is lower alkyl;

$R_{11}$ and $R_{12}$ are H; and $R_3$ to $R_{10}$ are each independently H, alkyl, alkylcarboxy, alkenyl, alkenylcarboxy, aryl, alkylaryl, OH, alkoxy, nitro, halo, trihalomethyl, amide, carboxamide, carboxy, sulfonyl, sulfonamide, amino, and mercapto, wherein:

(a) when both $R_1$ and $R_2$ are methyl, at least one of $R_3$ to $R_{10}$ must be a group other than H; and (b) when both $R_1$ and $R_2$ are methyl, and $R_4$–$R_{10}$ are H, $R_3$ may not be 2-methylbut-2-en-4-yl; and (c) when both $R_1$ and $R_2$ are methyl, and $R_4$–$R_6$ and $R_8$–$R_{10}$ are H, $R_3$ and $R_7$ may not simultaneously be 2-methylbut-2-en-4-yl; and (d) when both $R_1$ and $R_2$ are methyl, and $R_3$–$R_4$, $R_6$–$R_8$ and $R_{10}$ are H, $R_5$ and $R_9$ may not simultaneously be 2-methylbut-2-en-4-yl.

20. The method of claim 16 wherein $R_4$ is 2-methylbut-2-en-4-yl and $R_3$ and $R_5$–$R_{10}$ are H; or $R_5$ is 2-methylbut-2-en-4-yl and $R_3$–$R_4$ and $R_6$–$R_{10}$ are H; or $R_6$ is 2-methylbut-2-en-4-yl, and $R_3$–$R_5$ and $R_7$–$R_{10}$ are H.

21. The method of claim 1 wherein the 2,5-bisindol-3-yl-1,4-quinone compound is selected from the group consisting of:

(a) 2,5-Diacetoxy-3,6-di-[2-(2-methylbut-2-en-4-yl) indol-3-yl]1,4-quinone;

(b) 2,5-Diacetoxy-3,6-di-[2-(3-methyl-n-butyl)indol-3-yl]1,4-quinone;

(c) 2,5-Dihydroxy-3,6-di-[2-(3-methyl-n-butyl)indol-3-yl]1,4-quinone;

(d) 3,6-Di-[5-(bromo)indol-3-yl]-2,5-dihydroxy-1,4-quinone;

(e) 3,6-Di-[2-(allyl)indol-3-yl]-2,5-dihydroxy-1,4-quinone;

(f) 2,5-Dihydroxy-3,6-di-[2-(n-propyl)indol-3-yl]1,4-quinone;

(g) 3,6-Di-[2-(aminocarbonyl)indol-3-yl]-2,5-dihydroxy-1,4-quinone;

(h) 2,5-Diacetoxy-3,6-di-[2(aminocarbonyl)indol-3-yl]-1,4-quinone;

(i) 3,6-Di-[2-allylindol-3-yl]-2,5-dibenzoyloxy-1,4-quinone;

(j) 2,5-Dihydroxy-3,6-di-[2-(cyano)indol-3-yl]1,4-quinone;

(k) 2,5-Dihydroxy-3,6-di-[4-(methoxycarbonyl)indol-3-yl]1,4-quinone;

(l) 2,5-Dihydroxy-3,6-di-[5,7-(dimethoxy)indol-3-yl]1,4-quinone;

(m) 2,5-Dihydroxy-3,6-di-[4, 7-(dimethoxy)indol-3-yl]1,4-quinone;

(n) 2,5-Dihydroxy-3,6-di-[5-(nitro)indol-3-yl]1,4-quinone;

(o) 3,6-Di-[4(4-chlorobenzoylamino)indol-3-yl]-2,5-dihydroxy-1,4-quinone;

(p) 3,6-di-[2-(4-chlorophenyl)indol-3-yl]-2,5-dihydroxy-1,4-quinone;

(q) 2,5-Dihydroxy-3,6-di-[2-(4-fluorophenyl)indol-3-yl]1,4-quinone;

(r) 2,5-Dihydroxy-3,6-di-[4,6-(dim ethoxy)indol-3-yl]1,4-quinone;

(s) 2,5-Dihydroxy-3,6-di-[2-(5-hydroxy-6-methoxy) indol-3-yl]1,4-quinone;

(t) 2,5-Dihydroxy-3,6-di-[4-(cyano)indol-3-yl]1,4-quinone;

(u) 2,5-Dihydroxy-3,6-di-[5-(4-trifluoromethylphenylaminocarbonyl)indol-3-yl]1,4-quinone;

(v) 2,5-Dihydroxy-3,6-di-[2-(4-trifluoromethylphenylaminocarbonyl)indol-3-yl]1,4-quinone;

(w) 3,6-Di-[2-(5-bromo-6-nitro)indol-3-yl]-2,5-dihydroxy-1,4-quinone;

(x) 2,5-Dimethoxy-3,6-di-[2-(2-methylbut-2-en-4-yl) indol-3-yl]1,4-quinone;

(y) 2,5-Dimethoxy-3,6-di-[2-(3-methyl-n-butyl)indol-3-yl]1,4-quinone; or a pharmaceutically acceptable salt thereof.

22. The method of claim 1 wherein the 2,5-bisindol-3-yl-1,4-quinone compound is selected from the group consisting of:

(a) 2,5-Dihydroxy-3,6-di-[2-(methyl)indol-3-yl]-1,4-quinone;

(b) 3,6-Di-(2-ethylindol-3-yl)-2,5-dihydroxy-1,4-quinone;

(c) 3,6-Di-(2-butylindol-3-yl)-2,5-dihydroxy-1,4-quinone;

(d) 3,6-Di-[2-(but-1-en-4-yl)indol-3-yl]-2,5-dihydroxy-1,4-quinone;

(e) 2,5-Dihydroxy-3, 6-di-[2-(2-methylbut-1 -en-4-yl) indol-3-yl]-1,4-quinone;

(f) 2,5-Dihydroxy-3,6-di-[2-(4-methyl-n-pentyl)indol-3-yl]-1,4-quinone;

(g) 2,5-Dihydroxy-3,6-di-[2-(2-phenylethyl)indol-3-yl]-1,4-quinone;

(h) 3,6-Di-[(5-carboxy-2-ethyl)indol-3-yl]-2,5-dihydroxy-1,4-quinone;

(i) 3,6-Di-[[5-carboxy-2-(n-propyl)]indol-3-yl]-2,5-dihydroxy-1,4-quinone;

(j) 3,6-Di-[[5-carboxy-2-(3-methyl-n-butyl)]indol-3-yl]-2,5-dihydroxy-1,4-quinone;

(j) 3,6-Di-[2-(4-carboxy-n-butyl)indol-3-yl]-2,5-dihydroxy-1,4-quinone;

(k) 3-[[5-Carboxy-2-(3-methyl-n-butyl)]indol-3-yl]-2,5-dihydroxy-6-(indol-3-yl) 1,4-quinone;

(l) 3,6-Di-[(5-amino-2-ethyl)indol-3-yl]-2 ,5-dihydroxy-1,4-quinone;

(m) 3,6-Di-[[5-amino-2-(n-propyl)]indol-3-yl]-2,5-dihydroxy-1, 4-quinone;

(n) 3,6-Di-[5-amino-2-(3-methyl-n-butyl)]indol-3-yl]-2, 5-dihydroxy-1,4-quinone;

(o) 2,5-Diacetoxy-3,6-di-[2-(3-methyl-n-butyl)indol-3-yl]-1,4-quinone;

(p) 3,6-Di-[[2-ethyl-5-(4-methylphenylsulfonylamino)] indol-3-yl]-2,5-dihydroxy-1,4-quinone;

(q) 2,5-Dihydroxy-3,6-di-[[5-(4-methylphenylsulfonylamino)-2-(n-propyl)]indol-3-yl]-1,4-quinone;

(r) 2,5-Dihydroxy-3,6-di-[[2-(3-methyl-n-butyl)-5-(4-methylphenylsulfonylamino)]indol-3-yl]-1,4-quinone;

(s) 2,5-Dihydroxy-3, 6-di-[2-(2-methylpent-2-en-5-yl) indol-3-yl]-1,4-quinone;

or a pharmaceutically acceptable salt thereof.

23. The method of claim 1 wherein the 2,5-bisindol-3-yl-1,4-quinone compound is a compound of the formula:

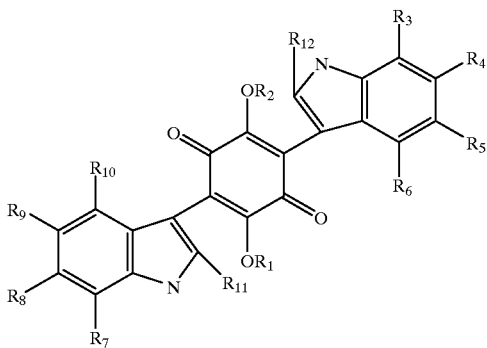

or a pharmaceutically acceptable salt thereof, wherein:

$R_1$ and $R_2$ are each independently hydrogen, lower alkyl, acetyl, aryl, alkylaryl or higher alkyl acid ester; and $R_3$ to $R_{10}$ are each independently H, alkyl, alkylcarboxy, aryl, alkylaryl, alkenyl, alkenylcarboxy, OH, alkoxy, nitro, halo, trihalomethyl, amide, carboxyamide, carboxy, sulfonyl, sulfonamide, amino, mercapto, 4-methylphenylsulfonylamino, or 2-methylbut-2-en-4-yl; and $R_{11}$ and $R_{12}$ are selected from the group consisting of hydrogen, methyl, ethyl, propyl, butyl, aryl, alkylaryl, alkylcarboxy, alkenylcarboxy, but-1-en-4-yl, 2-methylbut-1-en-4-yl, 4-methyl-n-pentyl, 2-phenylethyl, 2-methylpent-2-en-4-yl, and 4-carboxy-n-butyl, wherein at least one of $R_{11}$ and $R_{12}$ is other than hydrogen.

24. The method of claim 1 wherein the 2,5-bisindol-3-yl-1,4-quinone compound is a compound of the formula:

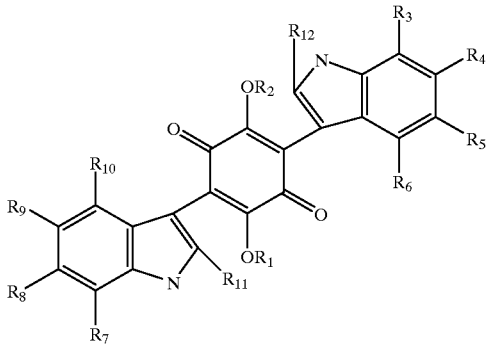

or a pharmaceutically acceptable salt thereof, wherein:

$R_1$ and $R_2$ are each independently hydrogen, lower alkyl, acetyl, aryl, alkylaryl or higher alkyl acid ester; and $R_3$ to $R_{10}$ are each independently H, alkyl, alkylcarboxy, aryl, alkylaryl, alkenyl, alkenylcarboxy, OH, alkoxy, nitro, halo, trihalomethyl, amide, carboxyamide, carboxy, sulfonyl, sulfonamide, amino, mercapto, 4-methylphenylsulfonylamino, or 2-methylbut-2-en-4-yl; and $R_{11}$ and $R_{12}$ are both 3-methyl-n-butyl.

25. The method of claim 1 wherein the 2,5-bisindol-3-yl-1,4-quinone compound is a compound of the formula:

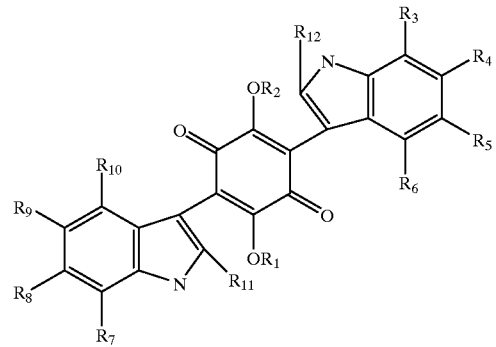

or a pharmaceutically acceptable salt thereof, wherein:

$R_1$ and $R_2$ are each independently hydrogen, lower alkyl, acetyl, aryl, alkylaryl or higher alkyl acid ester; and $R_3$ to $R_{10}$ are each independently H, alkyl, alkylcarboxy, aryl, alkylaryl, alkenyl, alkenylcarboxy, OH, alkoxy, nitro, halo, trihalomethyl, amide, carboxyamide, carboxy, sulfonyl, sulfonamide, amino, mercapto, 4-methylphenylsulfonylamino, or 2-methylbut-2-en-4-yl and wherein at least one of $R_3$ to $R_{10}$ is other than hydrogen;

and $R_{11}$ and $R_{12}$ are each independently hydrogen or 3-methyl-n-butyl.

* * * * *